United States Patent
Liang et al.

(10) Patent No.: US 8,071,105 B2
(45) Date of Patent: Dec. 6, 2011

(54) REISHI F3 SUB FRACTION POLYSACCHARIDES AND METHODS OF USING SAME

(75) Inventors: Shu-Mei Liang, Bethesda, MD (US); Yen-Po Chen, Kaohsing (TW); Wen-Bin Yang, Shenkeng Township (TW); Chi-Huey Wong, La Jolla, CA (US)

(73) Assignee: Academia Sinica, Taipei (TW)

( * ) Notice: Subject to any disclaimer, the term of this patent is extended or adjusted under 35 U.S.C. 154(b) by 338 days.

(21) Appl. No.: 12/244,709

(22) Filed: Oct. 2, 2008

(65) Prior Publication Data

US 2009/0263897 A1    Oct. 22, 2009

Related U.S. Application Data

(63) Continuation-in-part of application No. 12/107,030, filed on Apr. 21, 2008, now abandoned.

(60) Provisional application No. 61/058,538, filed on Jun. 3, 2008.

(51) Int. Cl.
*A61K 36/06* (2006.01)

(52) U.S. Cl. .................................. 424/195.15

(58) Field of Classification Search .............. None
See application file for complete search history.

(56) References Cited

U.S. PATENT DOCUMENTS

| | | | | |
|---|---|---|---|---|
| 4,522,811 A * | 6/1985 | Eppstein et al. | ............. | 514/2.4 |
| 5,334,704 A * | 8/1994 | Tsunoo et al. | ............. | 530/371 |
| 6,395,310 B1 * | 5/2002 | Iwasaki | ............. | 424/725 |
| 6,464,982 B1 * | 10/2002 | Lam | ............. | 424/195.15 |
| 6,471,860 B1 * | 10/2002 | Miltenyi et al. | ............. | 210/222 |
| 6,613,754 B1 * | 9/2003 | Wu | ............. | 514/54 |
| 7,135,183 B1 * | 11/2006 | Wang et al. | ............. | 424/195.15 |
| 7,323,176 B2 * | 1/2008 | Wang et al. | ............. | 424/195.15 |
| 2003/0012798 A1 * | 1/2003 | Ikekawa et al. | ............. | 424/400 |
| 2003/0068329 A1 * | 4/2003 | Kosuna et al. | ............. | 424/195.15 |
| 2003/0095981 A1 * | 5/2003 | Wong et al. | ............. | 424/195.15 |
| 2004/0018210 A1 * | 1/2004 | Hajjaj et al. | ............. | 424/195.15 |
| 2007/0072247 A1 * | 3/2007 | Wong et al. | ............. | 435/7.2 |
| 2007/0104729 A1 * | 5/2007 | Wang et al. | ............. | 424/195.15 |
| 2007/0105814 A1 * | 5/2007 | Hua et al. | ............. | 514/54 |
| 2007/0231339 A1 * | 10/2007 | Yu et al. | ............. | 424/184.1 |
| 2007/0298049 A1 * | 12/2007 | Tominaga et al. | ............. | 424/195.15 |
| 2008/0214442 A1 * | 9/2008 | Yu et al. | ............. | 514/8 |
| 2008/0247989 A1 * | 10/2008 | Shih et al. | ............. | 424/85.2 |
| 2009/0291100 A1 * | 11/2009 | Tominaga et al. | ............. | 424/195.15 |

OTHER PUBLICATIONS

Mizuno et al. Nippon Nogeikagaku Kashi (J. Agric. Chem. Soc. Japan) 1985, vol. 59, No. 11, pp. 1143-1151, BIOSIS Abstract.*

* cited by examiner

*Primary Examiner* — Christopher R. Tate

(74) *Attorney, Agent, or Firm* — Shantanu Basu; Eckman Basu LLP

(57) ABSTRACT

The present disclosure relates to the discovery of methods of isolating subfractions of an F3 Reishi extract, and of administration of these novel isolates to eukaryotic cells in order to induce certain immunomodulatory, hematopoeitic and tumor-inhibiting phenotypic changes in those eukaryotic cells, mediated through particular toll-like receptor (TLR) and other transmembrane receptors. F3 subfractions F301 and F331 have demonstrated that F331 is capable of activating at least TLR-2 while F301 is capable of activating at least TLR-2, TLR-4, and TLR-5.

18 Claims, 17 Drawing Sheets

Figure 1. F3 activates NFkB via TLR2 and TLR5.

Figure 2. TLR2 and TLR5 mediated NFkB activation induced by F3 is dependent on F3 dosage and TLR expression level.

(a)
Figure 3
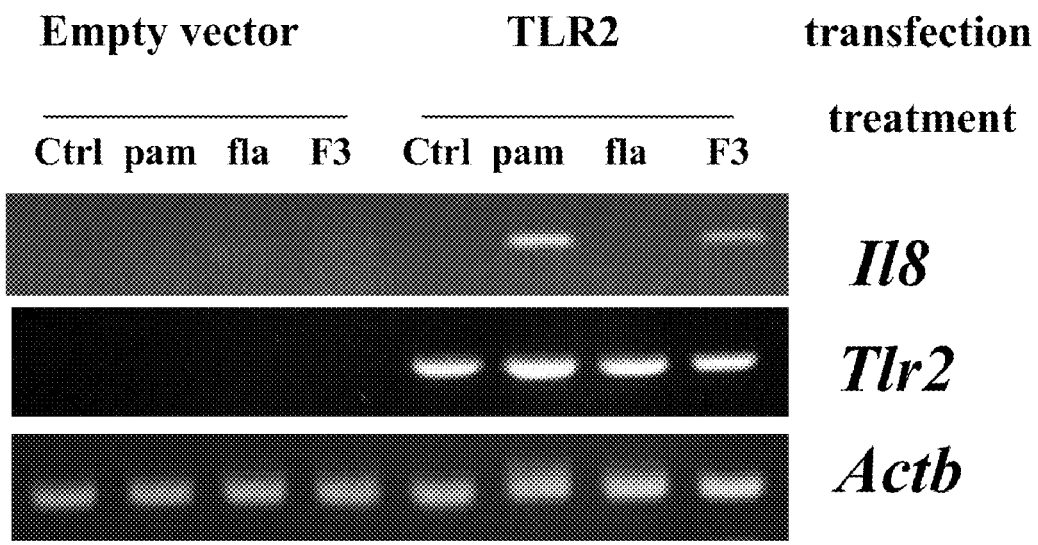
(b)
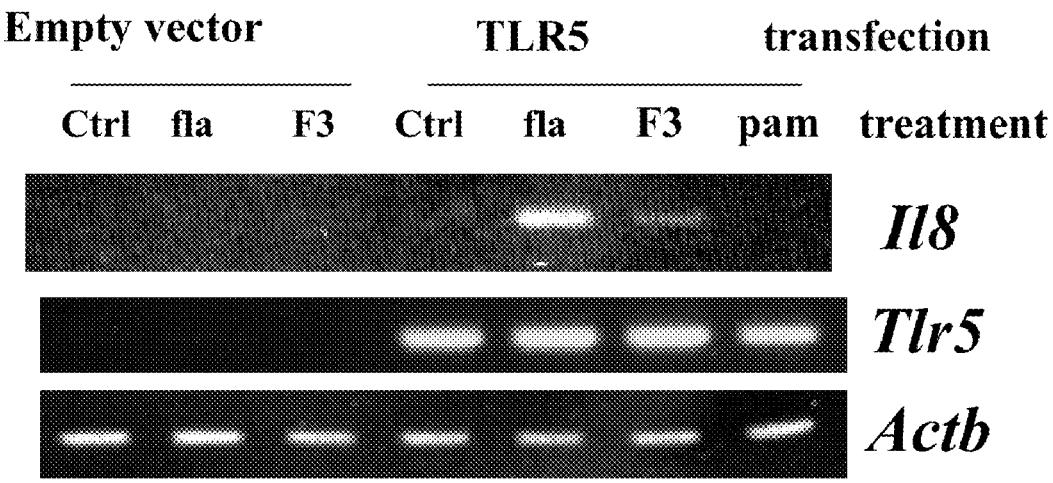
Figure 3. F3 induces IL-8 mRNA transcription via (a) TLR2 and (b) TLR5.

Figure 4. F3 induces IL-8 production via (a) TLR2 and (b) TLR5.

Figure 5
(a)
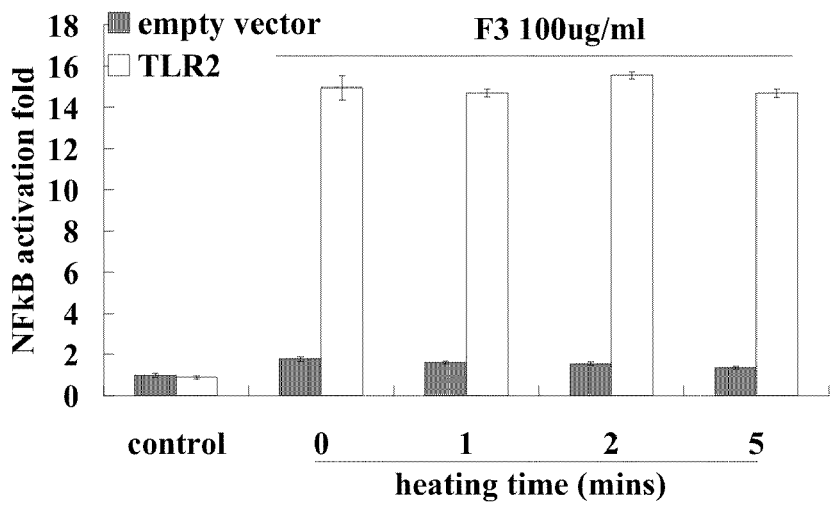
(b)
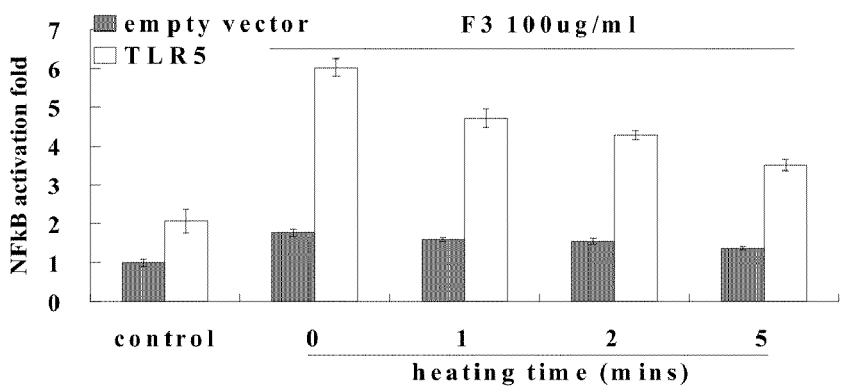
Figure 5. Heat effect on TLR2 or TLR5 mediated NFkB activation induced by F3.

Figure 6. NFkB activation induced by F3 via TLR2 or TLR5 is blocked by specific TLR antibody.

Figure 7. The effects of F3 subfractions, F301 and F331, on NFkB activation mediated by TLR2 or TLR5.

Figure 8. The effects of F301 subfractions on NFkB activation mediated by TLR2 or TLR5.

Figure 9. The effects of F331 subfractions on NFkB activation mediated by TLR2 or TLR5.

Figure 10
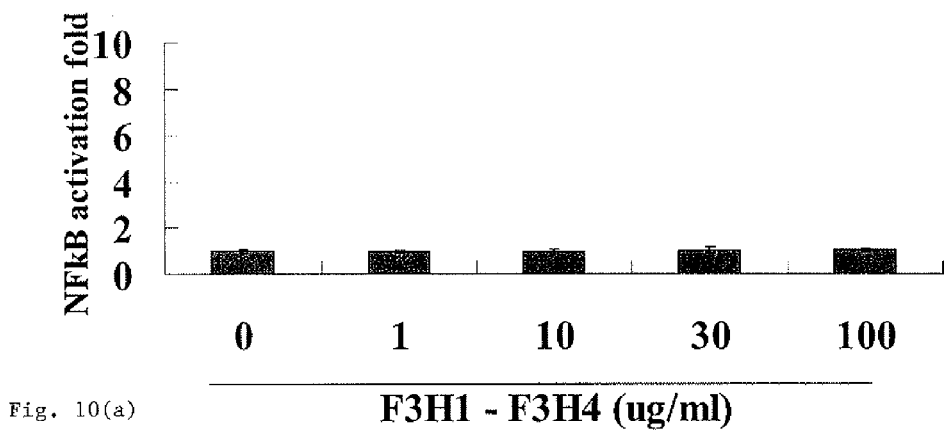
Fig. 10(a)
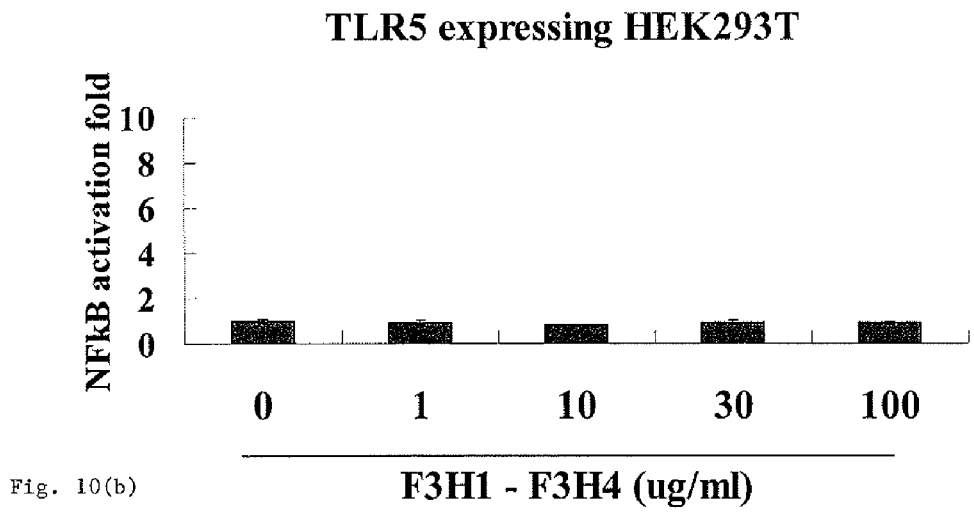
Fig. 10(b)
Figure 10. Beta (1,3) glycan backbone fragments less than 5 kD in weight (F3-H1 - F3-H4) do not induce TLR-2 or TLR-5 mediated increased activation of intracellular NF-κB.

FIGURE 11
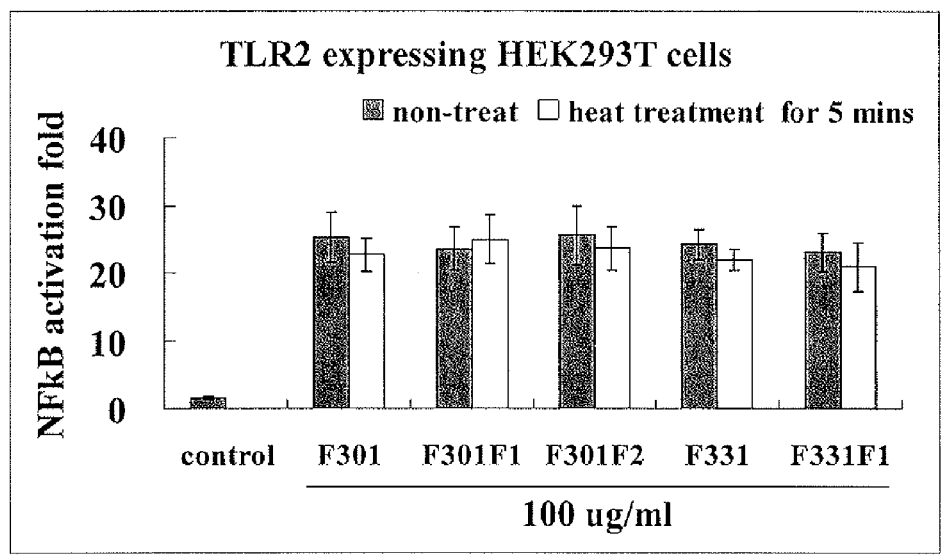
Fig. 11(a)
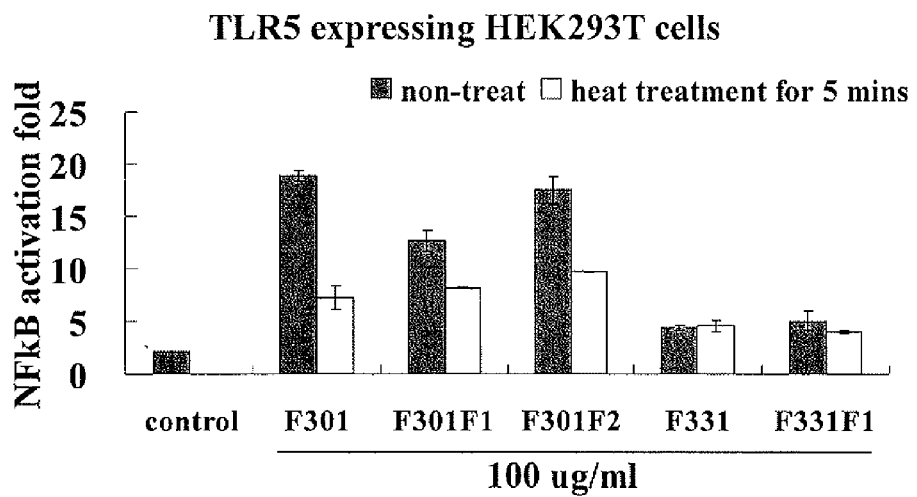
Fig. 11(b)
Figure 11. Heat effect on TLR2 or TLR5 mediated NFkB activation induced by F3 subfractions.

FIGURE 13a-b
(a)
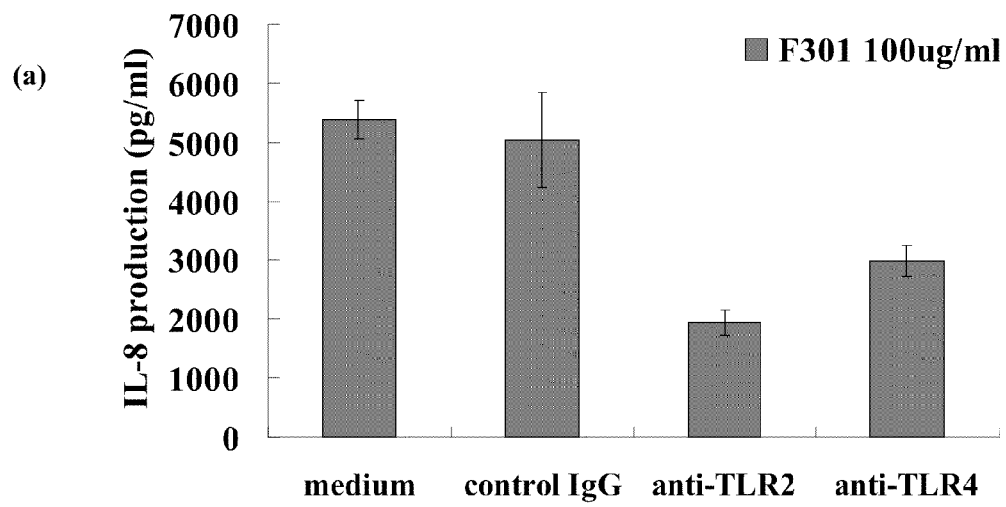
(b)
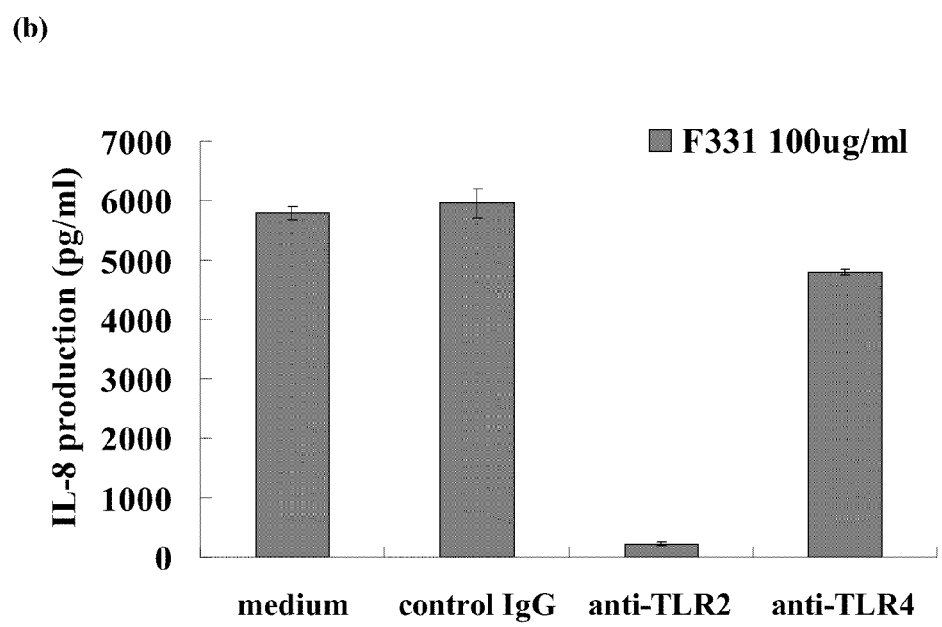

FIGURE 14a-b
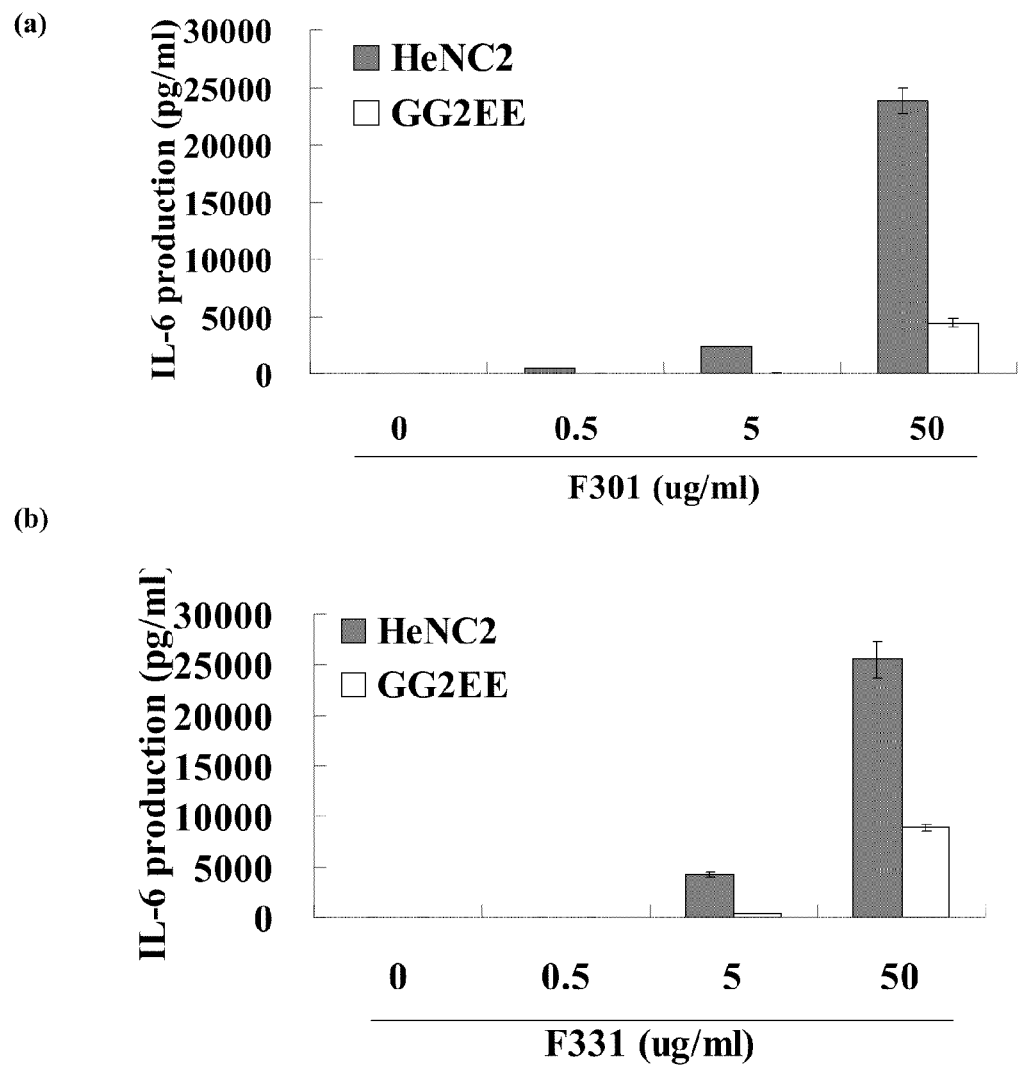

REISHI F3 SUB FRACTION POLYSACCHARIDES AND METHODS OF USING SAME

This application claims the Paris Convention priority and is a continuation-in-part of U.S. Utility patent application Ser. No. 12/107,030, filed Apr. 21, 2008, now abandoned and U.S. Provisional Patent Application Ser. No. 61/058,538, filed Jun. 3, 2008, the disclosures of which are incorporated herein by reference in their entirety.

BACKGROUND OF THE DISCLOSURE

The present disclosure provides medicinally active extracts, fractions and more specifically subfractions of Reishi and methods of preparing the same, from components of *Ganoderma lucidum* and *Ganoderma tsugae*, otherwise known as "Reishi" in order to induce certain immunomodulatory, hematopoeitic and tumor-inhibiting phenotypic changes in those eukaryotic cells, mediated through particular toll-like receptor (TLR) and other transmembrane receptors.

GENERAL BACKGROUND

*Ganoderma lucidum* (Reishi or Ling-Zhi) has been used in traditional Chinese medicine (TCM) as an anti-tumor and immunomodulating agent.

Polysaccharides from Reishi have been known to induce human PBMC proliferation and phenotypic and functional maturation of DCs with significant IL-12 and IL-10 production. In addition, it has been found in microarray analysis that genes associated with phagocytosis (CD36, CD206, and CD209) are decreased and genes associated with proinflammatory chemokines (CCL20, CCL5, and CCL19), cytokines [interleukin (IL)-27, IL-23A, IL-12A, and IL-12B], and costimulatory molecules (CD40, CD54, CD80, and CD86) are increased. See U.S. Pat. No. 7,135,183.

Treatment of dendritic cells with extract of reishi mycelium results in enhanced cell-surface expression of CD80, CD86, CD83, CD40, CD54, and human leukocyte antigen (HLA)-DR, as well as the enhanced production of interleukin (IL)-12p70, p40, and IL-10 and also IL-12p35, p40, and IL-10 mRNA expression. Some of these immune responses have been attributed to the activation of Toll-like receptor 4 (TLR-4). Given the variety of cell-surface receptor expression and activation and increased mRNA expression and cytokine translation observed, it is likely that other TLRs are capable of mediating reishi extract's physiological effects.

For example, IL-8 is a chemokine known to promote neutrophil chemotaxis and infiltration. Macrophages and endothelial cells secrete IL-8 in order to attract neutrophils and allow them to adhere to vascular endothelial cells. This helps the neutrophils migrate and enter the tissue where they are needed especially during inflammation and infection. Neutrophils are the first line of defense against invading bacteria.

Toll-like receptor agonists are being developed for the treatment of cancer, allergies and viral infections, and as adjuvants for potent new vaccines to prevent or treat cancer and infectious diseases. As recognition grows of the role of Toll-like receptor stimulation in inflammation and autoimmunity, TLR agonists can produce strikingly different responses when administered by different routes, doses and times.

For example, although inflammation characterizes most TLR responses, recent studies suggest an important role of TLR signaling for homeostasis in mucosal tissues. The intestinal tract is unique in that it is continually exposed to high concentrations of TLR ligands from commensal bacteria and yet manages to avoid the chronic inflammation that such ligands would provoke in any other organ. Continued TLR signaling has been demonstrated to be necessary for the integrity of the intestinal epithelium and protection from inflammation-mediated damage. For example, certain TLRs are associated with particular cell types. For example, TLR agonists may have a therapeutic effect on Inflammatory Bowel Disease (IBD).

For example, TLR-5 is often expressed on the cell surface of monocytes, immature dendritic cells and intestinal epithelial cells (IEC). For example, TLR-5 may also have antitumor activity, however, administration of TLR-5 agonists needs to be carefully evaluated in light of the known toxicity and adaptive immune response trigger role of known TLR-5 agonists such as flagellin.

For example, use of the HEK293T cell line transfected with TLR2 or TLR5 plasmid together with NF-κB-luc reporter plasmid provides a method to assay which ligands interact with specific TLR cell-surface receptors in order to mediate increased activation of intracellular NF-κB. Activated intracellular NF-κB is then capable of upregulating cytokine and chemokine mRNA transcription and, ultimately, translation of proteins corresponding to the transcribed mRNAs. Since HEK293T epithelial cells, unlike, for example, macrophages, do not produce IL-6 and TNF-α, IL-8 can be used as a marker to show that components of the F3 fraction of reishi extract can interact with transfected TLR2 and TLR5 receptors on cell surfaces in order to mediate intracellular NF-κB activation, which activated NK-κB can subsequently increase the transcription (as determined by RT-PCR) of mRNA coding for various cytokines and the translation of mRNAs to cytokine proteins as determined by ELISA. As activated NF-κB is known to upregulate transcription and translation of a variety of cytokines, TLR-2 and TLR-5 agonists capable of upregulating IL-8 transcription in transfected HEK-293T cells in vitro are also capable of upregulating other cytokines, such as IL-6 and TNF-alpha, whether assessed in epithelial or other cell types and whether assessed in vitro or in vivo.

SUMMARY OF THE DISCLOSURE

The present disclosure relates to the discovery of methods of isolating certain novel constituents of Reishi extract, and of subsequent administration of these novel isolates to eukaryotic cells in order to induce certain immunomodulatory, hematopoeitic and tumor-inhibiting phenotypic changes in those eukaryotic cells, mediated through particular toll-like receptor (TLR) and other transmembrane receptors.

Recently, a fucose-containing glycoprotein fraction (F3) was isolated from Reishi extract. Accumulate evidence shows that F3 modulates immune functions through TLR 4 and 2, and further study revealed that F3 activates not only TLR-2 and -4 but also TLR-5. The F3 extract was subfractioned and two components (F301 and F331) have been identified.

F301 and F331 have been identified. By at least one of relative hydrophobicity, total sugar content, and percentages of fucose, glucosamine, galactose, Glucose and mannose.

We have demonstrated that F331 is capable of activating at least TLR-2 while F301 is capable of activating at least TLR-2, TLR-4, and TLR-5.

In some exemplary implementations a method is disclosed of administering a sufficient amount of an F301 extract to at least one member of the group consisting of eukaryotic cells and eukaryotic cell-based organisms (including but not limited to eukaryotic cells and eukaryotic cell-based organisms includes dendritic, epithelial, and monocyte cells and cellular precursors); wherein the administered F301, increases toll-like receptor mediated activation of intracellular nuclear factor-kappa B by at least 5% when assayed by Reporter Gene Assay. In some instances the toll-like receptor mediated activation of intracellular nuclear factor-kappa B is mediated at least through the TLR-5 receptor. In some instances the toll-like receptor mediated activation of intracellular nuclear factor-kappa B is mediated at least through the TLR-2 receptor.

In some exemplary implementations a method is disclosed administering a sufficient amount of F301 to at least one member of the group consisting of eukaryotic cells and eukaryotic cell-based organisms; wherein the administered F301, increases toll-like receptor mediated transcription of messenger RNA coding for cytokines by at least 5% when assayed by RT-PCR. In some instances the toll-like receptor increased transcription of messenger RNA coding for cytokines is mediated at least through the TLR-5 receptor. In some instances the toll-like receptor increased transcription of messenger RNA coding for cytokines is mediated at least through the TLR-2 receptor. In some instances the increased toll-like receptor mediated transcription of messenger RNA coding results in an increase of mRNA coding for cytokines selected from the group consisting of interleukin-6, interleukin-8, and tumor necrosis factor-alpha.

In some exemplary implementations a method is disclosed administering a sufficient amount of F301 to at least one member of the group consisting of eukaryotic cells and eukaryotic cell-based organisms; wherein the administered F301, increases toll-like receptor mediated translation of messenger RNA to cytokines by at least 5% when assayed by ELISA. In some instances the toll-like receptor mediated increased translation of messenger RNA to cytokines is mediated at least through the TLR-5 receptor. In some instances the toll-like receptor mediated increased translation of messenger RNA to cytokines is mediated at least through the TLR-2 receptor. In some instances the increased toll-like receptor mediated translation of messenger RNA to cytokines results in an increase in production of intracellular and/or extracellular cytokines selected from the group consisting of interleukin-6, interleukin-8, and tumor necrosis factor-alpha.

In some exemplary implementations a product is disclosed formed by the process of homogenizing tissue of a *Ganoderma lucidum*; extracting the homogenized tissue with 0.1 N NaOH aqueous alkaline solution to form a crude extract; subjecting the crude extract to gel filtration chromatography using a Sephacryl S-500 column and eluting with an aqueous Tris buffer solution to form at least one fraction comprising a polysaccharide or glycopeptide component having terminal fucose residues; dialyzing at least one of the fractions containing a glycopeptide or polysaccharide component having a terminal fucose residue; precipitating the dialyzed fraction by adding ethanol to the dialyzed fraction; and resuspending the precipitate in an aqueous solution. In some instances the glycopeptide or polysaccharide component having a terminal fucose residue comprises at least about 37% total sugar; and, the percentages of the individual sugars fucose, glucosamine, galactose, Glucose and mannose are substantially fucose (3%), glucosamine (5%), galactose (9%), Glucose (74%), and mannose (9%). In some instances the glycopeptide or polysaccharide component having a terminal fucose residue comprises at least about 19% total sugar; and, the percentages of the individual sugars fucose, glucosamine, galactose, Glucose and mannose are substantially fucose (3%), glucosamine (18%), galactose (7%), Glucose (59%), and mannose (13%).

In some exemplary implementations a method is disclosed administering a sufficient amount of F331 to at least one member of the group consisting of eukaryotic cells and eukaryotic cell-based organisms; wherein the administered F331, increases toll-like receptor mediated activation of intracellular nuclear factor-kappa beta by at least 5% when assayed by Reporter Gene Assay. In some instances the group consisting of eukaryotic cells and eukaryotic cell-based organisms includes dendritic, epithelial, and monocyte cells and cellular precursors. In some instances the toll-like receptor mediated activation of intracellular nuclear factor-kappa beta is mediated at least through the TLR-2 receptor.

In some exemplary implementations a method is disclosed administering a sufficient amount of F331 to at least one member of the group consisting of eukaryotic cells and eukaryotic cell-based organisms; wherein the administered F331, increases toll-like receptor mediated transcription of messenger RNA coding for cytokines by at least 5% when assayed by RT-pCR. In some instances the toll-like receptor increased transcription of messenger RNA coding for cytokines is mediated at least through the TLR-2 receptor. In some instances the increased toll-like receptor mediated transcription of messenger RNA coding results in an increase of mRNA coding for cytokines selected from the group consisting of interleukin-6, interleukin-8, and tumor necrosis factor-alpha.

In some exemplary implementations a method is disclosed administering a sufficient amount of F331 to at least one member of the group consisting of eukaryotic cells and eukaryotic cell-based organisms; wherein the administered F331, increases toll-like receptor mediated translation of messenger RNA to cytokines by at least 5% when assayed by ELISA. In some instances the toll-like receptor mediated increased translation of messenger RNA to cytokines is mediated at least through the TLR-2 receptor. In some instances the increased toll-like receptor mediated translation of messenger RNA to cytokines results in an increase in production of intracellular and/or extracellular cytokines selected from the group consisting of interleukin-6, interleukin-8, and tumor necrosis factor-alpha.

In some exemplary implementations a product is disclosed formed by the process of: homogenizing tissue of a *Ganoderma lucidum*; extracting the homogenized tissue with 0.1 N NaOH aqueous alkaline solution to form a crude extract; subjecting the crude extract to gel filtration chromatography using a Sephacryl S-500 column and eluting with an aqueous Tris buffer solution to form at least one fraction comprising a polysaccharide or glycopeptide component having terminal fucose residues; dialyzing at least one of the fractions containing a glycopeptide or polysaccharide component having a terminal fucose residue; precipitating the dialyzed fraction by adding ethanol to the dialyzed fraction; and evaporating the ethanol/aqueous solution.

In some exemplary implementations a composition or product is disclosed of an extract of Reishi differing from the F3 fraction (FIG. 15*a*) comprising substantially 37% total sugar; and, the percentages of the individual sugars fucose, glucosamine, galactose, Glucose and mannose are substantially fucose (4%), glucosamine (5%), galactose (9%), Glucose (74%), and mannose (9%)

In some exemplary implementations a composition or product is disclosed of an extract of Reishi differing from the F3 fraction (FIG. 15*a*) comprising substantially 19% total sugar; and, the percentages of the individual sugars fucose, glucosamine, galactose, Glucose and mannose are substantially fucose (3%), glucosamine (18%), galactose (7%), Glucose (59%), and mannose (13%).

DRAWINGS OF THE PRESENT DISCLOSURE

The above-mentioned features and objects of the present disclosure will become more apparent with reference to the following description taken in conjunction with the accompanying drawings wherein like reference numerals denote like elements and in which:

FIGS. 3 and 4 depict relative amounts of cytokine production mediated by TLR-2 and TLR-5 potentiated NF-κB activation. FIGS. 3(a)-3(b) depict the expression levels of interleukin-8 mRNA analyzed by reverse transcription polymerase chain reaction (RT-PCR), while FIGS. 4(a)-4(b) depict amounts (pg/ml) of interleukin-8 produced in culture medium measured by ELISA.

FIGS. 5(a)-(b) depict the effect of heat pretreatment on the ability of Reishi F3 fraction to facilitate TLR-2 or TLR-5 mediated activation of intracellular NF-κB. As seen in FIG. 5(a), the ability of TLR-2 to mediate F3-dependent activation of intracellular NF-κB is largely unaffected by heat treatment of Reishi F3. As seen in FIG. 5(b), the ability of TLR-5 to mediate F3-dependent activation of intracellular NF-κB is increasingly diminished by longer heat treatment of Reishi F3.

Figure 6:
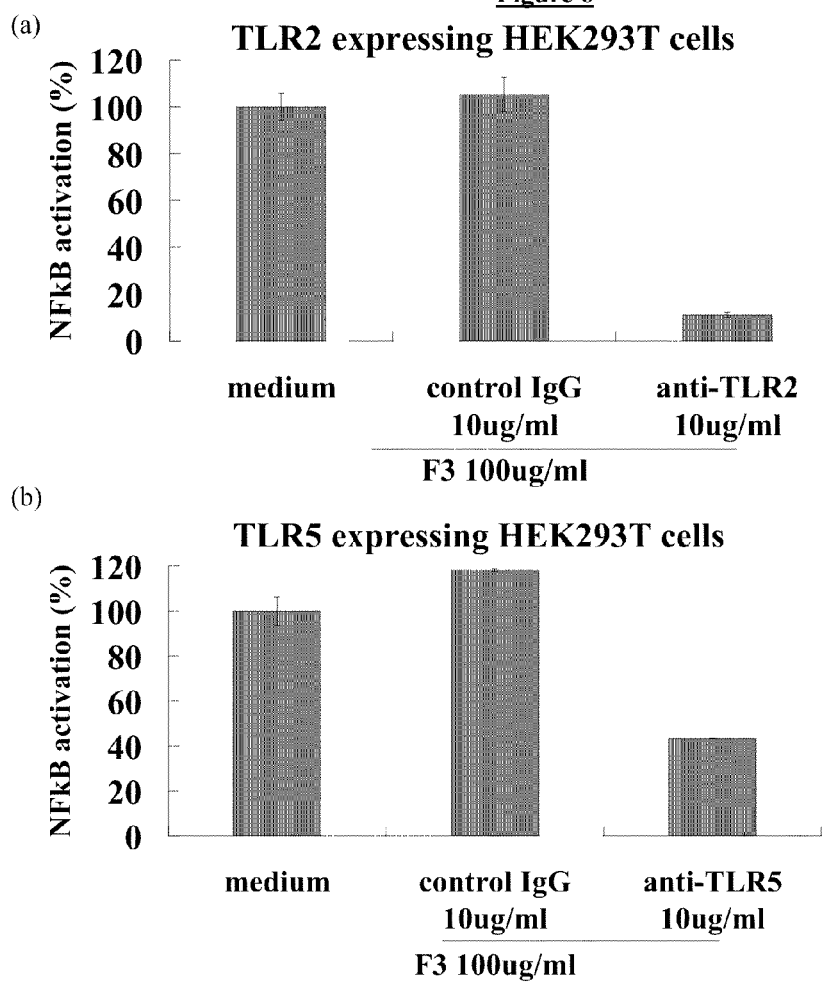

FIG. 6 depicts specific inhibition by TLR antibodies of F3-dependent, TLR-2 (FIG. 6a) or TLR-5 (FIG. 6b) mediated activation of intracellular NF-κB.

Figure 7:
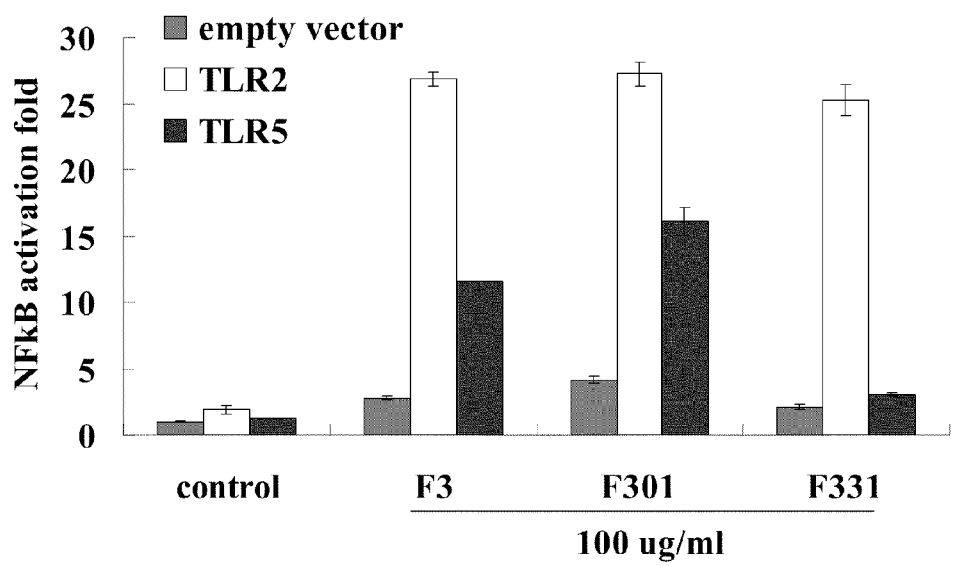

FIG. 7 depicts TLR-2 and/or TLR-5 mediated activation of intracellular NF-κB by specific subfractions of Reishi F3 fraction. As shown, F301 is capable of inducing both TLR-2 and TLR-5 mediated activation of intracellular NF-κB. F331, by contrast, induces only TLR-2 mediated activation of intracellular NF-κB.

Figure 8:
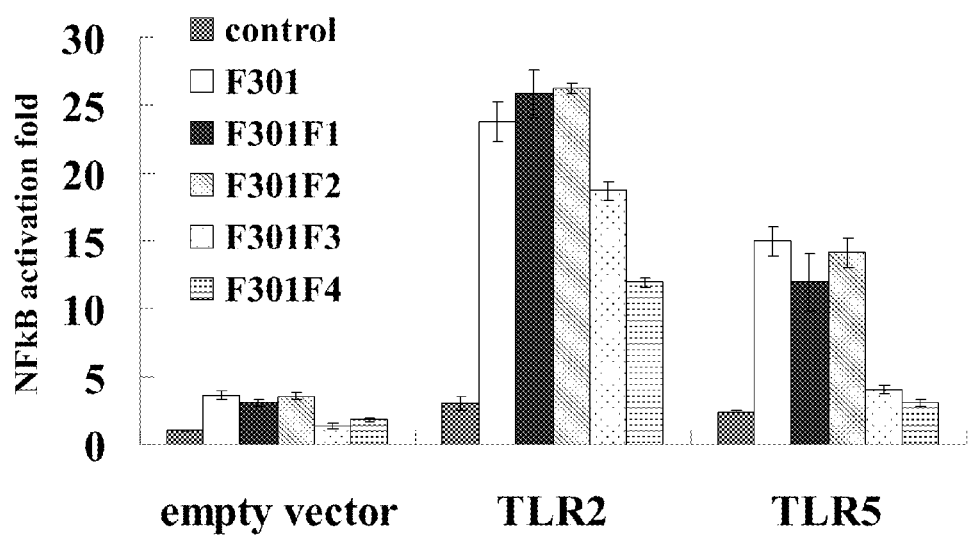

FIG. 8 depicts F301 subfractions capable of initiating TLR-2 and TLR-5 mediated activation of intracellular NF-κB.

Figure 9:
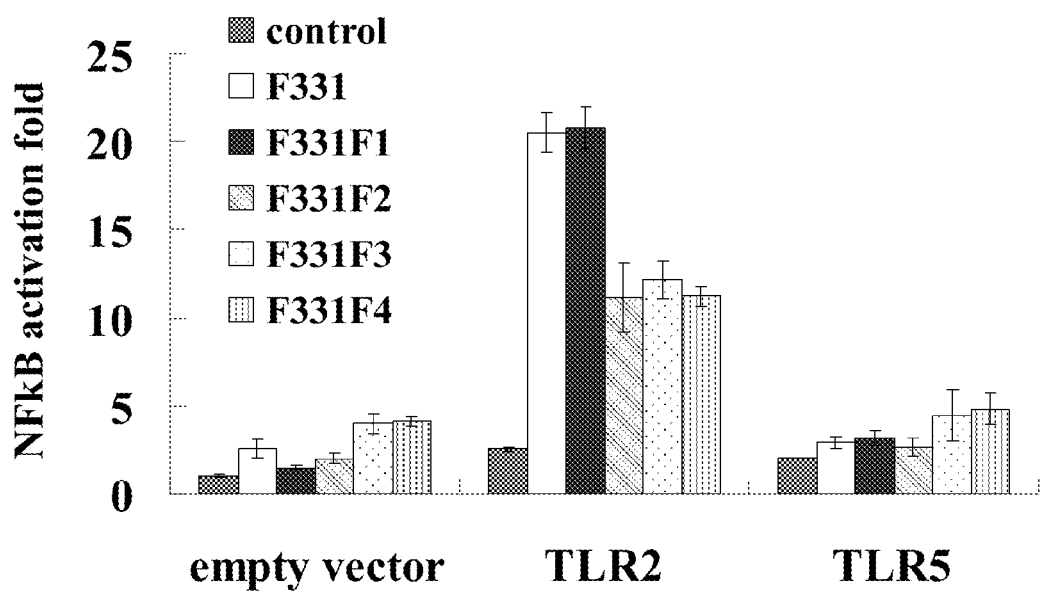

FIG. 9 depicts F331 subfractions capable of initiating TLR-2 dependent activation of intracellular NF-κB.

FIGS. 10(a) and (b) demonstrate that beta(1,3)glycan backbone fragments less than 5 kD in weight do not induce TLR-2 or TLR-5 mediated increased activation of intracellular NF-κB.

FIGS. 11(a) and (b) demonstrate that F301 and F331 subfractions are capable of inducing TLR-2 mediated increased activation of intracellular NF-κB, regardless of whether the F301 or F331 are previously heat treated (FIG. 11(a)). FIG. 11(b) demonstrates that F301 subfractions are capable of inducing TLR-5 mediated activation of intracellular NF-κB. Heat treated F301 subfractions and F331 subfractions (whether heat treated) are less capable of inducing such TLR-5 mediated activation.

Figure 12:
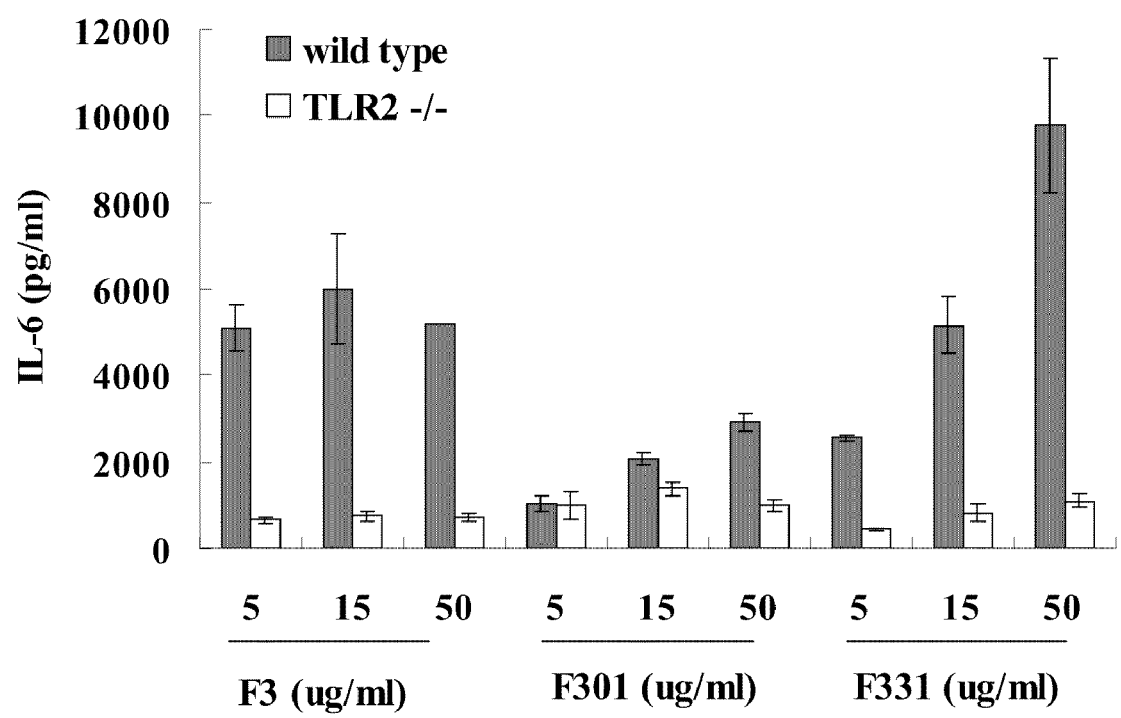

FIG. 12 demonstrates that F3, F301, and F331-instigated IL-6 production is decreased in peritoneal macrophages substantially lacking TLR-2 receptors, indicating TLR-2's role in mediating F3, F301, and/or F331-mediated IL-6 upregulation.

FIGS. 13a-b demonstrate that both F-301 and F-331 are capable of upregulating TLR-2 and TLR-4-mediated IL-8 production, as treatment with anti-TLR-2 or TLR-4 antibodies leads to a decrease in relative IL-8 upregulation.

FIGS. 14a-b demonstrate that both F301 and F331 are capable of initiating TLR-4-mediated upregulation of IL-6. Wild-type macrophage cells exhibited TLR-4-mediated upregulation of IL-6 in the presence of F301 or F331, while mutant macrophage cells expressing defective TLR-4 exhibited a relative decrease in IL-6 upregulation.

Figure 15A:
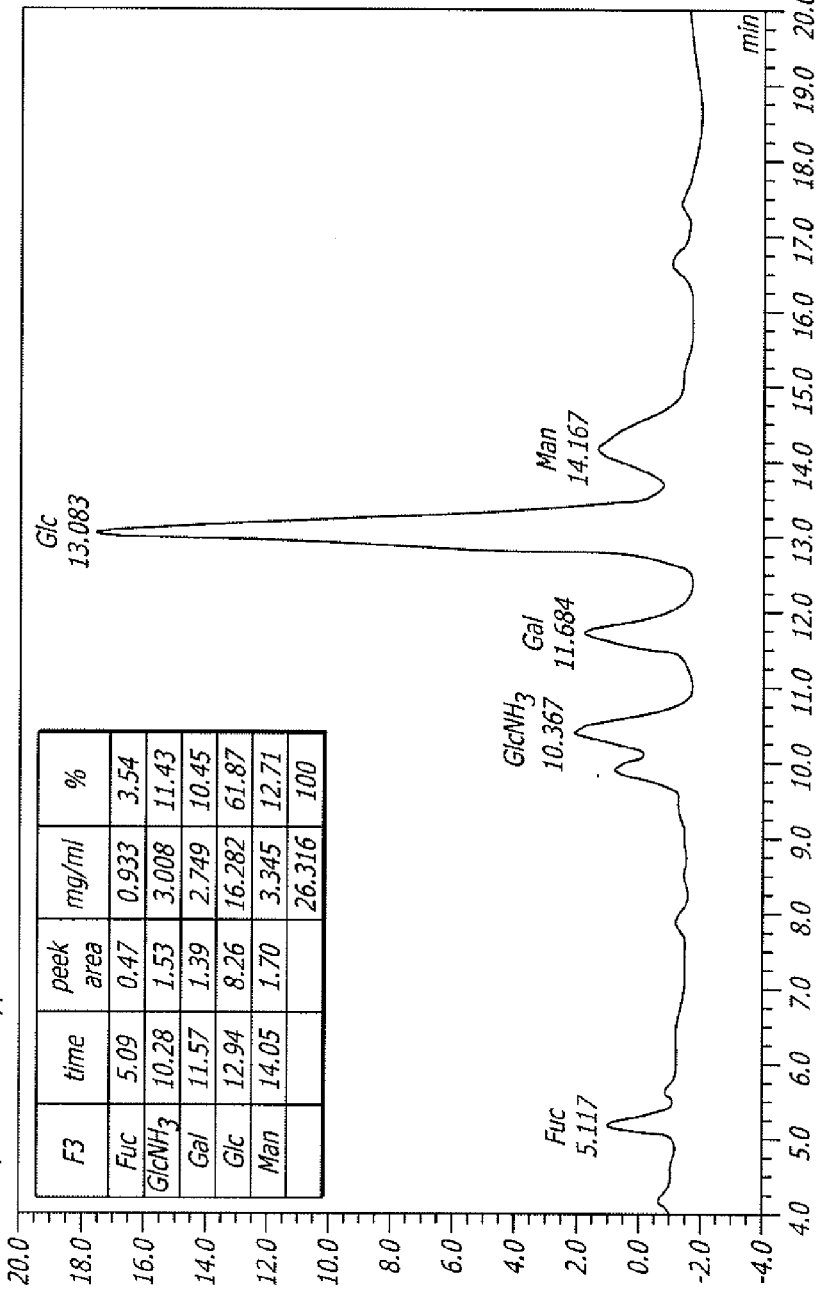
Figure 15B:
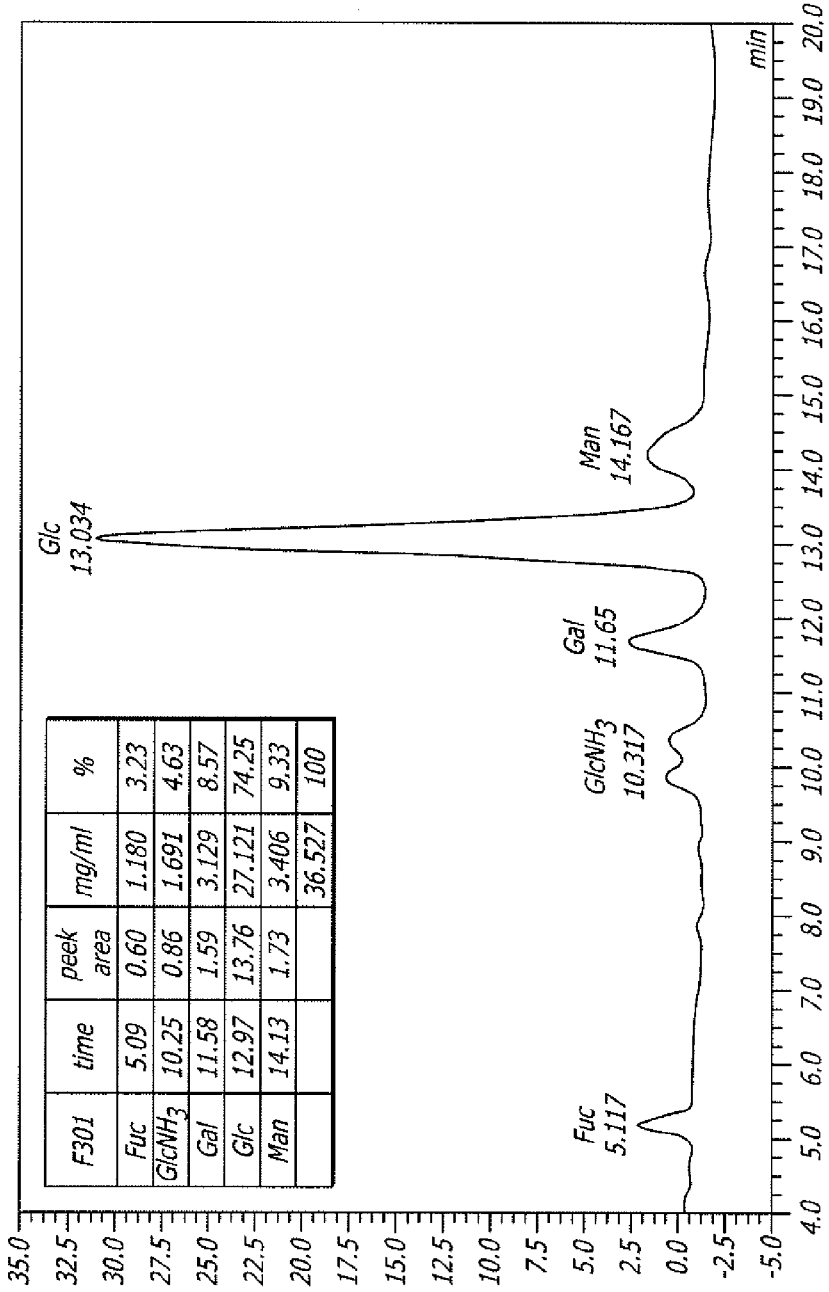
Figure 15C:
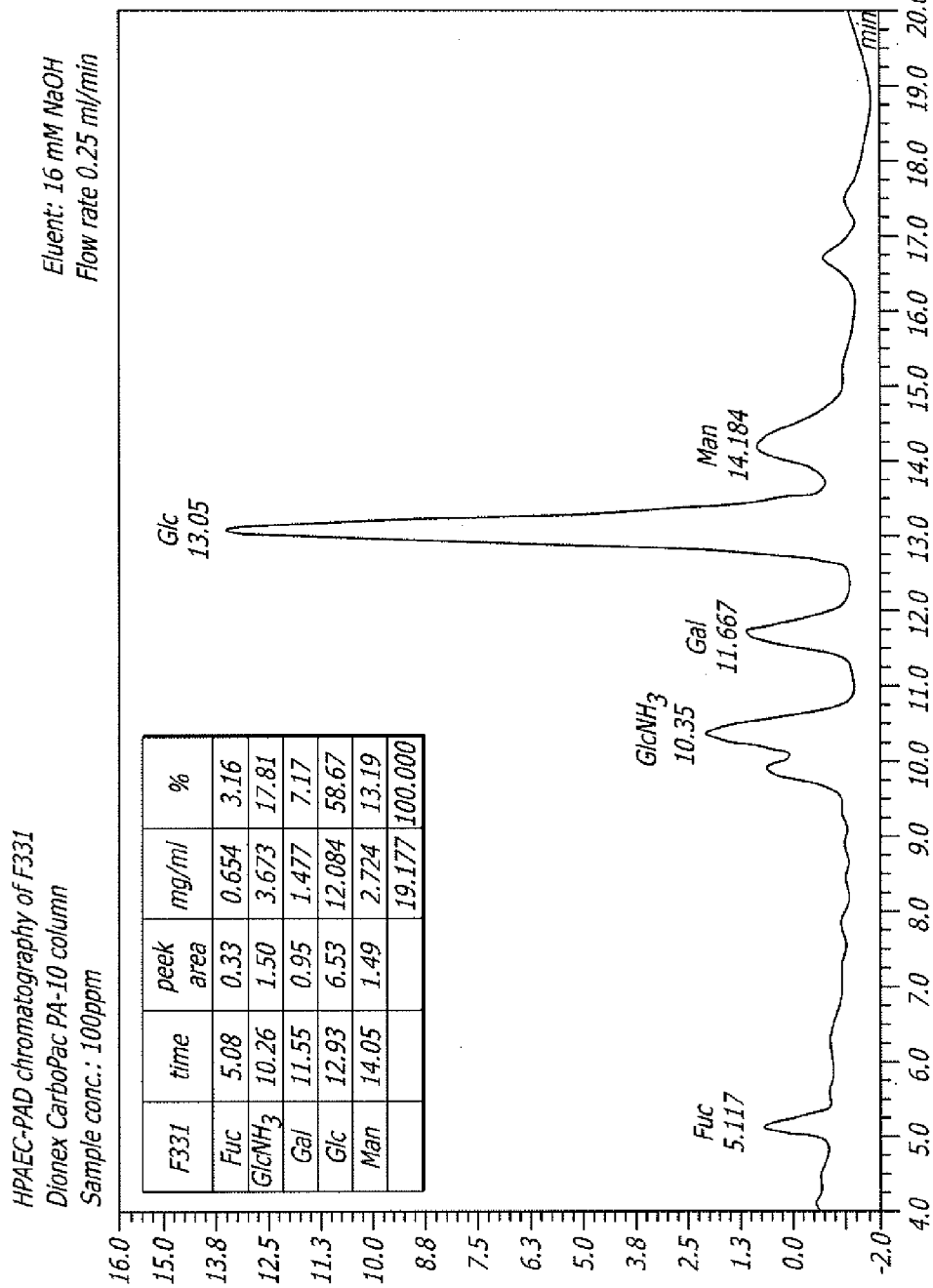

FIGS. 15a-c show HPAEC-PAD chromatography of F3, F301 and F331.

DETAILED DESCRIPTION

For the purposes of describing the present invention, the following terms are intended to refer to the associated definitions as described below:

"Activation of NF-κB (nuclear factor-kappa B)" means the process by which stimulation of NF-κB mediated by Toll-like receptors activates NF-κB, subsequently facilitating increased transcription of mRNA coding for intracellular production of particular chemokines and cytokines and subsequent translation of the transcribed mRNA, resulting in increased amounts of particular cytokines and chemokines that are both present intracellularly and released by the eukaryotic cell into the intercellular environment. Activation of NF-κB may be measured directly via plasmid reporter assay or indirectly through measurement of NF-κB-upregulated transcription (e.g. mRNA, measurable through RT-PCR) or translation (e.g. protein, measurable through ELISA) products.

"Administering" means in vitro or in vivo administration, wherein in vivo administration may encompass oral, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection and infusion as well as co-administration as a component of any medical device or object to be inserted (temporarily or permanently) into the body.

"CD" means cluster of differentiation, a protocol used for the identification and investigation of cell surface molecules present on leukocytes. CD molecules can act in numerous ways, often acting as receptors or ligands. A signal cascade is usually initiated upon CD-ligand interaction, altering the behavior of the cell. Some CD proteins do not play a role in cell signaling, but have other functions, such as cell adhesion.

"Cell Surface Markers" means a protein that is present in the cell surface of a eukaryotic cell, as well as any gene expression product specific to that particular protein (whether characterized in vivo or in vitro) (for example, mRNA or cDNA).

"Centrifuge" means an apparatus consisting essentially of a compartment spun about a central axis to separate contained materials of different specific gravities, or to separate colloidal particles suspended in a liquid.

"Chemokine" means any of a family of small proteins intracellulary produced and stored and extracellularly secreted by eukaryotic cells. Proteins are classified as chemokines according to shared structural characteristics such as small size (they are all approximately 8-10 kilodaltons in size), and the presence of four cysteine residues in conserved locations that are key to forming their 3-dimensional shape. Their name is derived from their ability to induce directed chemotaxis in nearby responsive cells; they are a chemotactic subset of the cytokine family.

"Chemotaxis" is a migratory response elicited by chemicals. A concentration gradient of chemicals developed in a fluid phase guides the vectorial movement of responder cells or organisms. Inducers of locomotion towards increasing steps of concentrations are considered as chemoattractants, while chemorepellents result moving off the chemical. Chemotaxis is performed on Transwell filter support (Corning). Collagen is coated on the sides of transfilters onto which cells will be seeded. Human intestinal epithelial cell line CaCo-2 is seeded onto Transwell filter support in inverted direction for 21 to 28 days for differentiation until transepithelial resistance is above 300 $\Omega cm^2$. F3 or it's subfractions are added at apical site of well-differentiated CaCo-2 cells for 2 days. Human neutrophils isolated from fresh blood by Ficoll method are added at the basolateral site of CaCo-2 cells which have treated with F3 or it's subfractions. After 1 hour incubation in 37□ and 5% CO2, the neutrophils infiltrating from the basolateral site to apical site are quantified by myeloperoxidase activity. (Reference: Lee, W. Y., A. C. Chin, S. Voss and C. A. Parkos. 2006. Methods in Molecular Biology 341: 205-215.)

"Cytokine" means any of a group of proteins and peptides that are used in organisms as signaling compounds. These chemical signals are similar to hormones and neurotransmitters and are used to allow one cell to communicate with another.

"Dendritic Cells" means immune cells that form part of the mammalian immune system. Their main function is to process antigen material and present it on the surface to other cells of the immune system, thus functioning as antigen-presenting cells.

"Dendritic Cell Markers" means any of a group of cell surface molecules found generally on the surface of dendritic cells.

"Differentiate" means the process by which eukaryotic cells acquire a "type" (e.g. dendritic cell, chondrocyte); e.g. a change in cellular morphology without a requirement of a change in genetic material.

"ELISA" means Enzyme-Linked ImmunoSorbent Assay, a biochemical technique used mainly in immunology to detect the presence of an antibody or an antigen in a sample. ELISA has been used as a diagnostic tool in medicine and plant pathology, as well as a quality control check in various industries. In simple terms, in ELISA an unknown amount of antigen is affixed to a surface, and then a specific antibody is washed over the surface so that it can bind to the antigen. This antibody is linked to an enzyme, and in the final step a substance is added that the enzyme can convert to some detectable signal.

"Endothelial" means the thin layer of cells that line the interior surface of blood vessels, forming an interface between circulating blood in the lumen and the rest of the vessel wall.

"Epithelial" means any of a group of cells that line the cavities and surfaces of structures throughout the body. It is also the type of tissue of which many glands are formed. Epithelium lines both the outside (skin) and the inside cavities and lumen of bodies. The outermost layer of our skin is composed of dead stratified squamous, keratinized epithelial cells.

Mucous membranes lining the inside of the mouth, the esophagus, and part of the rectum are lined by nonkeratinized stratified squamous epithelium. Other, open to outside body cavities are lined by simple squamous or columnar epithelial cells.

Other epithelial cells line the insides of the lungs, the gastrointestinal tract, the reproductive and urinary tracts, and make up the exocrine and endocrine glands. The outer surface of the cornea is covered with fast-growing, easily-regenerated epithelial cells.

Functions of epithelial cells include secretion, absorption, protection, transcellular transport, sensation detection, and selective permeability.

"Expression" means the process by which inheritable information which comprises a gene, such as the DNA sequence, is made manifest as a physical and biologically functional gene product, such as protein or RNA. Expression may be quantitated by immunological (e.g. MACS, FACS) and/or by molecular biology (e.g. total RNA analysis) techniques.

"F3" means a main fraction of crude Reishi extract, as can be obtained via gel filtration chromatography of crude Reishi extract using a Sephacryl S-500 column eluted with 0.1 N Tris buffer (pH 7.0) and subsequent to determination of the sugar content of the fraction via anthrone analysis or phenol-sulfuric acid method.

"F301" means a water soluble, hydrophilic fraction of F3 sequential extraction, separable from F331 by, in one example, precipitating F301 from a hydrophobic solution.

"F331" means a soluble fraction in ethanol/water=3/1, generally hydrophobic fraction of F3 sequential extraction, separable from F301 by, in one example, maintaining in solution in a F301-precipitating hydrophobic solvent.

In addition F301 and F331 fractions of F3 (FIG. 15$a$) can be characterized by sugar composition analysis in which F301 and F331 were hydrolyzed by acid hydrolysis (4N HCl, 70° C., 6 h) and analyzed for monosaccharides composition using HPAEC-PAD (high pH anion exchange chromatography-pulsed amperometric detection) as shown in FIGS. 15$b$ and 15$c$. The "F301" measured by this method contained substantially 36.5% total sugar which composed of fucose (3%), glucosamine (5%), galactose (9%), Glucose (74%), and mannose (13%). The "F331" measured by this method contained substantially 19% total sugar which composed of fucose (3%), glucosamine (17%), galactose (7%), Glucose (59%), and mannose (13%). Measurements are not intended to be limiting rather they provide guidelines and may be biased, be substantially as measured or vary slightly from measurement to measurement due to a plethora of variables.

"Fibroblast" means a type of cell that synthesizes and maintains the extracellular matrix of many animal tissues. Fibroblasts provide a structural framework (stroma) for many tissues, and play a critical role in wound healing. They are the most common cells of connective tissue in animals.

"Gel filtration" means separation of proteins, peptides, and oligonucleotides on the basis of size. Molecules move through a bed of porous beads, diffusing into the beads to greater or lesser degrees. Smaller molecules diffuse further into the pores of the beads and therefore move through the bed more slowly, while larger molecules enter less or not at all and thus move through the bed more quickly. Both molecular weight and three dimensional shapes contribute to the degree of retention. Gel Filtration Chromatography may be used for analysis of molecular size, for separations of components in a mixture, or for salt removal or buffer exchange from a preparation of macromolecules.

"Glycoconjugate" means a type of compound consisting of carbohydrate units covalently linked with other types of chemical constituent.

"Glycoprotein" means proteins that contain oligosaccharide chains (glycans) covalently attached to their polypeptide backbones.

"Glycoside" means certain molecules in which a sugar part of the molecule is bound to some other part of the molecule.

"Glycosylation" means the process or result of addition of saccharides to proteins and lipids.

"HEK-293T" means a human fibroblast-derived and immortalized cell line particularly amenable to transfection in vitro.

"Increased Expression of Cell Markers" means an increased quantity of a particular type of cell surface protein or mRNA molecule coding for that particular type of cell surface protein. Various protein molecules are associated with particular eukaryotic cell morphologies. Increased expression may be assayed using antibody-linked cell sorting ("FACS") or through magnetic-activated cell sorting ("MACS"). Alternately, increased expression may be assayed by use of RT-PCR, in which the quantity of intracellular expression of mRNA coding for production of a particular type of CD molecule is indirectly determined.

"Increased Transcription" means increased intracellular production of mRNA by a subject over a control subject, measured through RT-PCR.

"Increased Translation" means increased intracellular production of a protein of interest by a subject over a control subject, measured through ELISA.

"Infiltration" means the diffusion or accumulation (in a tissue or cells) of substances (e.g. neutrophils) not normal to it or in amounts in excess of the normal.

"Interleukin" means any of a group of cytokines (secreted signaling molecules) that were first seen to be expressed by white blood cells (leukocytes, hence the -leukin) as a means of communication (inter-). The function of the immune system depends in a large part on interleukins, and rare deficiencies of a number of them have been described, all featuring autoimmune diseases or immune deficiency. Interleukins are commonly designated using an abbreviation: e.g. IL-1, IL-2, etc.

"Lyophilize" means a freeze-drying dehydration process typically used to preserve a perishable material or make the material more convenient for transport. Freeze drying works by freezing the material and then reducing the surrounding pressure and adding enough heat to allow the frozen water in the material to sublime directly from the solid phase to gas.

"Macrophage" means cells within the tissues that originate from specific white blood cells called monocytes. Monocytes and macrophages are phagocytes, acting in nonspecific defense (or innate immunity) as well as specific defense (or cell-mediated immunity) of vertebrate animals. Their role is to phagocytose (engulf and then digest) cellular debris and pathogens either as stationary or mobile cells, and to stimulate lymphocytes and other immune cells to respond to the pathogen.

"Mature Dendritic Cells" means dendritic cells that have come into contact with a pathogen and are capable of presenting pathogen protein fragments at their cell surfaces.

"Mononuclear cells" or "monocytes" means large, phagocytic mononuclear leukocytes produced in the vertebrate bone marrow and released into the blood and tissues where they develop into macrophages; contain a large, oval or somewhat indented nucleus and surrounded by voluminous cytoplasm and numerous organelles. For purposes of describing the present invention, mononuclear cells includes mononuclear cells in vitro, in vivo and in vivo but subsequently isolated and extracted.

"Morphology" means the outward appearance (shape, structure, color, pattern) and/or identity of a eucaryotic cell, organism, or organism component.

"mRNA" means Messenger Ribonucleic Acid. mRNA is a molecule of RNA encoding a chemical "blueprint" for a protein product.

"NF-κB (nuclear factor-kappa B)" means a protein complex which is a transcription factor. NF-κB is found in almost all animal cell types and is involved in cellular responses to stimuli such as stress, cytokines, free radicals, ultraviolet irradiation, oxidized LDL, and bacterial or viral antigens. NF-κB plays a key role in regulating the immune response to infection. Consistent with this role, incorrect regulation of NF-κB has been linked to cancer, inflammatory and autoimmune diseases, septic shock, viral infection and improper immune development. NF-κB has also been implicated in processes of synaptic plasticity and memory.

"PBMNC" means a peripheral blood-derived mononuclear cell.

"PBS" means Phosphate-Buffered Saline, a buffer.

"Purified Reishi" means a reishi extract prepared as described in U.S. Nonprovisional application Ser. No. 11/553,402 and/or 10/213,257 (now U.S. Pat. No. 7,135,183), incorporated by reference herein, wherein the purified reishi is comprised of a polysaccharide or glycopeptide containing terminal fucose residues.

"Reishi" means the name for one form of the mushroom *Ganoderma lucidum*, and its close relative *Ganoderma tsugae*.

"RT-PCR" means reverse transcription polymerase chain reaction (RT-PCR), a laboratory technique for amplifying a defined piece of a ribonucleic acid (RNA) molecule. The RNA strand is first reverse transcribed into its DNA complement or complementary DNA, followed by amplification of the resulting DNA using polymerase chain reaction. This can either be a 1 or 2 step process "Subject" means, but is not limited to, any eukaryotic cell or eukaryotic cell-based organism, whether administered in vivo or in vitro to that cell or cell-based organism.

"Suspension Cells" means incubated eukaryotic cells that have not adhered to the sides of the incubation vessel.

"Toll-like Receptor" means any of a class of single membrane-spanning non-catalytic receptors that recognize structurally conserved molecules derived from microbes once they have breached physical barriers such as the skin or intestinal tract mucosa, and activate immune cell responses.

"Transfection" means the introduction of foreign material into eukaryotic cells using a virus vector or other means of transfer. The term transfection for non-viral methods is most often used in reference to mammalian cells, while the term transformation is preferred to describe non-viral DNA transfer in bacteria and non-animal eukaryotic cells such as fungi, algae and plants.

Transfection of animal cells typically involves opening transient pores or 'holes' in the cell plasma membrane, to allow the uptake of material. Genetic material (such as supercoiled plasmid DNA or RNA constructs), or even proteins such as antibodies, may be transfected. In addition to electroporation, transfection can be carried out by mixing a cationic lipid with the material to produce liposomes, which fuse with the cell plasma membrane and deposit their cargo inside.

"0.1 N Tris buffer" means a buffer solution.

Detailed exemplary implementations of the present invention are disclosed herein; however, it is to be understood that the disclosed exemplary implementations are merely illustrative of the invention that may be embodied in various forms. In addition, each of the examples given in connection with the various exemplary implementations of the invention are intended to be illustrative, and not restrictive. Further, the figures are not necessarily to scale, and some figures may be exaggerated to show details of particular components. Therefore, specific structural and functional details disclosed herein are not to be interpreted as limiting, but merely as a representative basis for teaching one skilled in the art to variously employ the present invention.

In one exemplary implementation, a method is disclosed comprising homogenizing reishi tissue; dissolving the reishi extract in water; stirring the reishi extract/water mixture for at least about 24 hours while maintaining the temperature of the reishi extract/water mixture at a temperature of at least about 4° Celsius; centrifuging the reishi extract/water mixture for a sufficient amount of time to remove insoluble materials; evaporating water from the centrifuged reishi extract/water mixture at a temperature of at least about 35° Celsius in order to remove at least a portion of the water from the reishi extract/water mixture; and purifying the reishi extract.

In another exemplary implementation, the resultant concentrated reishi extract/water mixture is lyophilized and subsequently resuspended in a liquid phase.

In another exemplary implementation, the resuspended reishi extract is subsequently purified.

In another exemplary implementation, purification of the resuspended reishi extract further involves subjecting the resuspended reishi extract to gel filtration chromatography using a Sephacryl S-500 column and eluting with an aqueous Tris buffer solution to form one or more filtered fractions having terminal fucose residues.

In another exemplary implementation, purification of the filtered fraction includes precipitating the resuspended F3 (reishi F3 fraction) in a 75% ethanol and 25% $H_2O$ solution so as to separate hydrophilic (in precipitate) and hydrophobic (in supernatant) components of the resuspended reishi extract.

In another exemplary implementation, the separated hydrophilic and hydrophobic components of the resuspended F3 (reishi F3) are further subfractionated using any of a number of separation techniques known in the art.

In another exemplary implementation, the lyophilized reishi extract is resuspended in 0.1 N Tris buffer.

In another exemplary implementation, the lyophilized reishi extract is resuspended and the resultant liquid suspension is adjusted to a pH of 7.0.

In another exemplary implementation, the resuspended reishi extract is purified by use of gel filtration.

In another exemplary implementation, the resuspended reishi extract gel filtration is collected as a series of fractions.

In another exemplary implementation, the filtration fractions are subsequently subfractionated, for example, by hydrolysis of the filtration fraction and subsequent filtration.

In another exemplary implementation, each collected fraction or subfraction of F3 is subsequently separated into hydrophilic and hydrophobic components and thereafter optionally subfractionated, as described above.

In another exemplary implementation, each collected fraction is subjected to anthrone analysis or the phenol-sulfuric acid method in order to detect sugar components.

In another exemplary implementation, the filtered resuspended reishi extract is dialyzed to remove excessive salt.

In another exemplary implementation, the filtered resuspended reishi extract is re-lyophilized subsequent to filtration.

In another exemplary implementation, the reishi extract is F3.

In another exemplary implementation, the reishi extract is F301 or a subfraction of F301.

In another exemplary implementation, the reishi extract is F331 or a subfraction of F331.

In another exemplary implementation, the reishi extract is any of fractions F3-H1 to F3-H4.

In another exemplary implementation, the purified reishi extract (alone or in combination with other excipients) is administrable to a subject.

In another exemplary implementation, the subject is a eukaryotic cell or eukaryotic cell-based organism.

In another exemplary implementation, the purified reishi extract is administrable to a subject under in vitro or in vivo conditions.

In another exemplary implementation, the subject is any one or all of eukaryotic monocytes; epithelial cells; dendritic cells; macrophages, neutrophils, or any hematopoetic or transformative derivative of these cells.

In another exemplary implementation, the subject is a person in need of treatment.

In another exemplary implementation, a method is disclosed comprised of administering a sufficient amount of purified reishi extract to a subject so as to increase intracellular activation of NF-κB.

In another exemplary implementation, a method is disclosed comprised of administering a sufficient amount of purified reishi extract to a subject so as to increase toll-like receptor mediated transcription of mRNA coding for cytokines.

In another exemplary implementation, a method is disclosed comprised of administering a sufficient amount of purified reishi extract to a subject so as to increase toll-like receptor mediated translation of mRNA coding for cytokines to corresponding protein products.

In another exemplary implementation, any of the above methods result in an increase in activated NF-κB.

In another exemplary implementation, any of the above methods result in an increase in toll-like receptor mediated transcription of mRNA coding for cytokines.

In another exemplary implementation, any of the above methods result in an increase in toll-like receptor mediated translation of mRNA coding for cytokines to corresponding protein products.

In another exemplary implementation, any of the above methods result in an increase in cytokine production by a subject.

In another exemplary implementation, the increased cytokines and related upstream RNA and DNA products are selected from the group comprising IL-6, IL-8, TNF-alpha, and/or other known, proinflammatory cytokines.

In another exemplary implementation, any of the above methods result in increased cell surface expression of cell surface receptors.

In another exemplary implementation, any of the above methods result in an increased cell surface expression of cell surface receptors selected from the group comprising CD80, CD83, CD86, MHC class II receptors, and/or CCR-7.

In another exemplary implementation, increased cell surface expression of cell surface receptors and/or increased cytokine production is measurable by correlating such increase to an increase in any of the following intracellular events:

increase in Toll receptor dimerization;
increase in MAP kinase activation;
increase in cellular kinase phosphorylation;
increase in Toll receptor association with any or all downstream signal transduction constituents, including but not limited to p38; Erk, and/or Akt.

Materials and Methods of the Disclosure

Crude Reishi Extract. Crude Reishi extract (prepared via alkaline extraction (0.1 N NaOH), neutralization and ethanol precipitation) was obtained from Pharmanex Co. (CA, USA). Immobiline DryStrip (pH 3-10 NL (non-linear), 18 cm) and IPG buffer (pH 3-10 NL) were purchased from Amersham Pharmacia Biotech (Uppsala, Sweden). CHAPS, Tris buffer, agarose, iodoacetamide and alpha-cyano-4-hydroxycinnamic acid were from Sigma Co. (St. Louis, Mo., USA); dithioerythritol (DTE) was from Merck Co. (Darmstast, Germany); acrylamide, ammonium persulfate (APS) and TEMED were from Bio-Rad (Hercules, Calif., USA); sodium dodecyl sulfate (SDS) and glycine were from Fluka (Buchs, Switzerland); sequencing grade trypsin was from Promega (Madison, Wis., USA).

Purification of Reishi extract. Twenty eight mg of the crude extract were dissolved in 2 mL of Tris buffer (pH 7.0, 0.1 N) and centrifuged to remove the insoluble materials (7 mg). The supernatant was purified by gel filtration chromatography using a Sephacryl® S-500 column (100 cm×1.6 cm) with 0.1 N Tris buffer (pH 7.0) as the eluent. The flow rate was set at 0.5 mL/min, and 5.0 mL per tube was collected. After the chromatography, each fraction was subjected to anthrone analysis to detect sugar components. Five fractions were collected (fractions F1-F5), each dialyzed to remove excessive salt and lyophilized to give 1.0, 6.2, 5.3, 2.1, and less than 1 mg, respectively.

Anthrone colorimetric method. After the chromatography, each fraction was subjected to analysis to detect sugar components; e.g. by the phenol method described in *Bioorganic & Medicinal Chemistry*, 2002, 10:1057-62 and *Bioorganic & Medicinal Chemistry*, 2004, 12:5595-5601, each herein incorporated by reference. For example, each 1.5 mL of anthrone (9,10-dihydro-9-oxoanthracene) solution (0.2 g anthrone dissolved in 100 mL of conc. sulfuric acid) in a series of test tubes immersed in an ice water bath was carefully overlayed with 1.5 mL of sample (20-40 µg/mL of D-glucose or equivalent). After all additions had been made, the tubes were shaken rapidly and then replaced in an ice water bath. The tubes were heated for 5 min in a boiling water bath and then cooled; the optical densities were read within an hour at 625 nm against distilled water. Standards, reagent blanks and unknowns were run in triplicate because of likely contamination by other carbohydrate sources. Calculations were made on the basis that the optical densities are directly proportional to the carbohydrate concentration.

Preparation of Reishi polysaccharide F331 and F301. The Reishi polysaccharide F3 fraction (1.0 g) was dissolved in d.d-water (30 mL) and then 95% ethyl alcohol (90 mL) was added. The resulting solution was stood at 4° C., 12 h for precipitation. After centrifuged, the clean solution was dried in rotavaper and lyophilizer to give F331 (212 mg, 21%). The pellet was dissolved with d.d-water (30 mL) again and lyophilization to give water-soluble F301 (420 mg, 42%).

Preparation of Reishi polysaccharide subfractions F3H1-F3H4. The Reishi polysaccharide fraction F3 (250 mg) was hydrolyzed using 6M trifluoric acetic acid (10 mL) at 60° C. for 6 h. The solution hydrolyte was removed TFA in vacuum pump, adding 0.1N NaOH until solution became alkaline condition (pH≧7~8). The solution of crude hydrolyte was purified through a gel-filtration chromatography using a G-50 gel with d.d-water as the eluent. After the chromatography, each tube was subjected to sulfuric acid-phenol analysis to detect sugar components. Four fractions were collected, called F3H1 (5%), F3H2 (7%), F3H3 (8%) and F3H4 (10%) respectively, as low molecular weight β-D-glucans.

Reverse transcription (RT) and polymerase chain reaction (PCR). Human fibroblast-derived HEK293T cells were subjected to RNA extraction using Qiagen RNAeasy mini kit to obtain ~1 µg of the desired RNA. Reverse transcription (RT) was performed using the Thermoscript R/T PCR System, and the Thermoscript system protocol I, from Gibco BRL. The reaction was carried out as follows: 8 µL of RNA, 2 µL of primer (Oligo(dT)$_{20}$) (5'-TTTTTTTTTTTTTTTTTTTT-3' purchased from Invitrogen) 2 µL of 10 mM dNTP Mix, and DEPC H$_2$O (0.1% diethylpyrocarbonate-treated H$_2$O) was added to each tube, which was then incubated at 65° C. for 5 min and immediately put on ice. The following was added to each tube as a 8 µL mixture: 4 µL of 5×cDNA buffer, 1 µL of 0.1 M dithiothreitol (DTT), 1 µL of RNaseOut (a ribonuclease inhibitor) and 1 µL of Thermoscript R/T, and 1 µL of DEPC water. The mixture was incubated at room temperature for 10 min and then 55° C. for 30 min to allow first strand of cDNA synthesis. Enzyme activity was terminated by incubating the reactions at 85° C. for 5 min and the tubes were then placed on ice for 10 min. The samples were stored at −20° C. until used for PCR.

Each sample (3 µL) was added to each reaction tube and the following reagents were added as a 47 µL mix: 5 µL of 10×PCR buffer, 4 µL of 10 mM dNTP Mix, 2 µL of each primer (10 OD/mL, sense and anti-sense), 33 µL of DEPC H$_2$O, and 1 µL of ProZyme® (DNA polymerase, from PROtech Technology). Human IL-8 expression was detected by using specific primer (forward: 5'-atg act tcc aag ctg gcc gtg gct-3'; reverse: 5'-tct cag ccc tct tca aaa act tct c-3') with an initial denaturation step of 95° C. for 10 min, followed by 30 cycles of 95° C. for 45 sec, 55° C. for 45 sec, 72° C. for 1 min, and a final elongation step of 72° C. for 7 min. Human TLR2 and TLR5 expression were detected by using specific primers (hTLR2-forward: 5'-ggc cag caa att acc tgt gtg-3'; hTLR2-reverse: 5'-cca ggt agg tct tgg tgt tca-3'; hTLR5-forward: 5'-cat tgt atg cac tgt cac tc-3'; hTLR5-reverse: 5'-cca cca cca tga tga gag ca-3') with an initial denaturation step of 94° C. for 5 min, followed by 30 cycles of 94° C. for 30 sec, 55° C. for 30 sec, 72° C. for 1 min, and a final elongation step of 72° C. for 7 min. Human β-actin expression was detected by using PrimerScreen™ human β-actin primer pair (Biosource) with an initial denaturation step of 95° C. for 1 min 30 sec, followed by 35 cycles of 94° C. for 30 sec, 60° C. for 45 sec, 72° C. for 45 sec, and a final elongation step of 72° C. for 7 min. The reactions were analyzed by gel electrophoresis.

ELISA analysis. Ninety-six well MaxiSorp microplates (Nunc) were coated with anti-human IL-8 antibodies (Biosource) in coating buffer (8 g/L NaCl, 1.13 g/L Na$_2$HPO$_4$, 0.2 g/L KH$_2$PO$_4$, 0.2 g/L KCl, pH 7.4) at 4° C. overnight. After coating, the plates were washed with PBST (0.1% Tween20) then blocked by blocking buffer (0.1% Tween20, 0.5% BSA in PBS) for 1 hour. Supernatants from stimulated cells were added for 2 hour together with biotinylated anti-human IL-8 antibodies (Biosource) at room temperature. The plates were then washed and treated with streptavidin-HRP (Biosource) for 30 minutes at room temperature, followed by another washing and treated with TMB for 30 minutes at room temperature. The reaction was stopped by adding 1N H$_2$SO$_4$. The data were collected by measuring absorbance at 450 nM by ELISA reader (vMax, Molecular Devices). A standard curve generated using recombinant human IL-8 was used to determine cytokine concentration.

NFkB luciferase reporter gene assay. TLRs was transiently expressed in TLRs-lacking HEK293T cells and then assayed for their responsiveness to samples. HEK293T cells were transfected with TLR1 to TLR10 expressing plasmid and pcDNA3.1 as empty vector control; p5xNFkB-Luc, which contains a luciferase reporter gene regulated by the NF-kB binding sequence. The luciferase gene is expressed only when NF-kB binds to the binding sequence. To normalize the transfection efficiency, the cells were cotransfected with pcDNA3.1-β-gal. Plasmids were introduced into HEK293T cells by transfection using Lipofectamine2000 (Invitrogen). Briefly, HEK293T cells were cultured in a 96-well plate at a concentration of 2.5×10$^4$ cells per well in 0.1 ml culture medium at 37° C. overnight. Medium was replaced by Opti- MEMI (Invitrogen) just before transfection. The transfection mixture was prepared by diluting 0.3 µl of Lipofectamine2000 in 25 µl of OPTI-MEMI medium to which 0.1 µg of plasmid DNA (0.01 µg/well TLR expressing plasmid or pcDNA3.1 as empty vector, 0.07 µg/well p5xNFkB-luc reporter plasmid (Stratagene) and 0.02 µg/well pcDNA3.1-βgal) in 25 µl of OPTI-MEMI was then added. After 20 minutes incubation at room temperature, the transfection mixture was then added to the cells and mixed by gently shaking. After 24 hours of incubation at 37° C. in 5% CO2, the cells were stimulated with samples. After 6 hours, cells were lysed and assayed for luciferase activity using the luciferase assay system (Promega) according to the manufacturer's instructions. Cells were washed twice with 100 µl of PBS and lysed in 100 µl of passive lysis buffer (Promega). Twenty µl cell lysate was used to measure luciferase activity. The luciferase activity of each sample was normalized to the β-galactosidase activity. Experimental data were expressed as the fold increases over those of unstimulated control cells transfected with empty vector.

Beta-galactosidase activity was measured by adding cell lysate samples in 0.1M phosphate buffer containing 1 mM $MgCl_2$, 45 mM β-mercaptoethanol and 1 mg/ml ONPG at pH 7.5. Incubated in 37° C. for 30 to 60 min. The data were collected by measuring absorbance at 405 nM by ELISA reader (vMax, Molecular Devices).

Preparation Of Knockout Mice/Mutant v. Wild-Type TLR-4 Comparison. The strain of TLR2 knock-out mice we used in experiments is B6.129-Tlr2$^{tm1kir}$ which were purchased from The Jackson Laboratory. The TLR2 knock-out mice are generated by disrupting sequence of the C-terminus of the extracellular and part of the transmembrane domains of Tlr2 gene by a targeting vector containing neomycin resistance and herpes simplex virus thymidine kinase genes. The Wild-type mice we used in experiments are the same genetic background strain of TLR2 knock-out mice.

TLR4 mutant macrophage cell line. The TLR4 mutant macrophage cell line GG2EE was derived from bone marrow of a LPS unresponsive C3H/HeJ mouse strain and expressed a non-functional TLR4 containing a proline to histidine mutation at amino acid residue 714. The control wild type macrophage cell line HeNC2 was derived from bone marrow of C3H/HeN mouse strain and expressed functional TLR4. (Reference: Blasi, E., D. Radzioch, S. K. Durum and L. Varesio. 1987. European Journal of Immunology 17: 1491-1498.)

Figure 1:
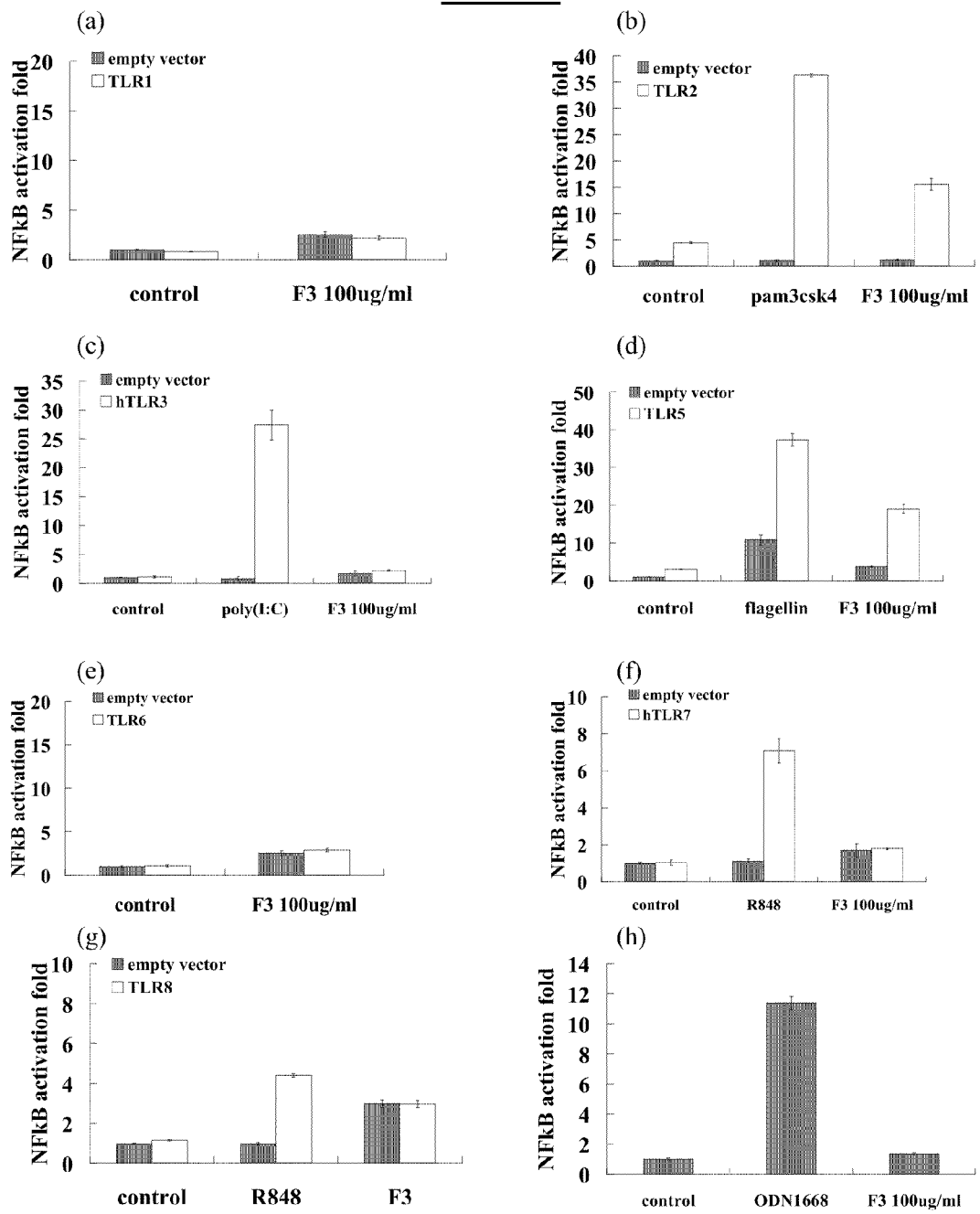
FIG. 1 is a graphic depiction of TLR-2 and/or TLR-5 mediated activation of intracellular NFκB potentiated by interaction of the F3 Reishi fraction with transfected transmembrane TLR-2 and TLR-5 receptors.

Results:

F3 activates intracellular NF-κB through both TLR-2 and TLR-5 receptors. FIG. 1 is a graphic depiction of TLR-2 and/or TLR-5 mediated activation of intracellular NFκB potentiated by interaction of the F3 Reishi fraction with transfected transmembrane TLR-2 and TLR-5 receptors.

Figure 2:
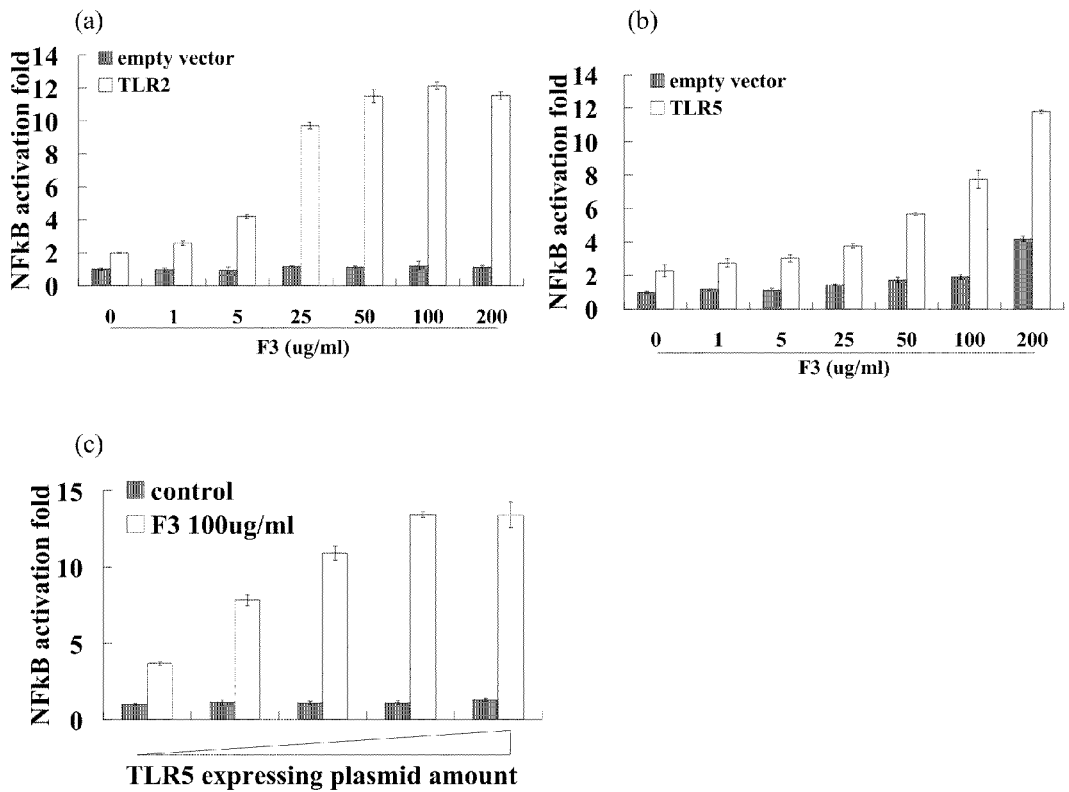
FIG. 2 is a graphic depiction of the extent to which TLR-2 and TLR-5 mediated NFκB activation induced by the F3 Reishi fraction is both F3 dose and TLR receptor expression dependent.

F3 induced activation of NF-kB mediated by TLR-2 and/or TLR-5 is also dose dependent and is dependent on both the concentration of TLR receptor agonist (F3) and on the level of TLR receptor expression on the cell surface. FIG. 2 is a graphic depiction of the extent to which TLR-2 and TLR-5 mediated NFkB activation induced by the F3 Reishi fraction is both F3 dose and TLR receptor expression dependent.

Figure 4:
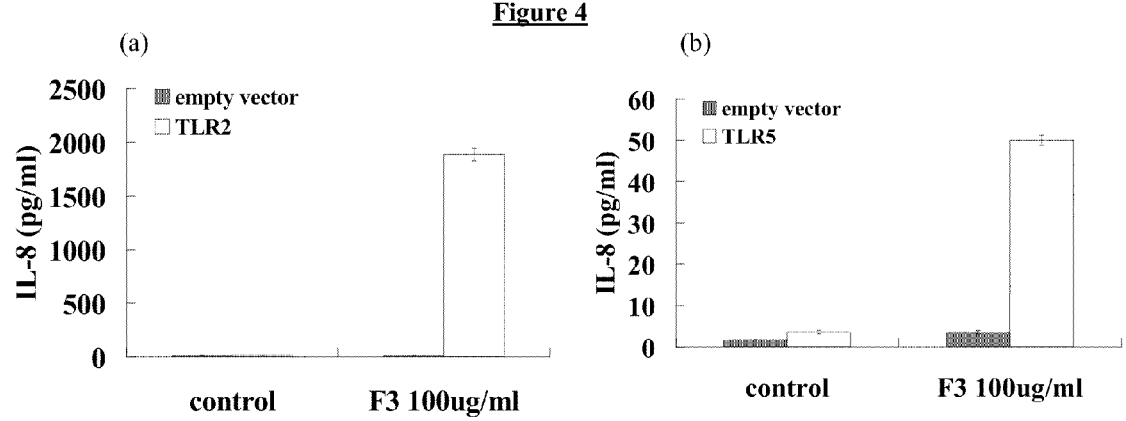

F3 also induces increased transcription of mRNA coding for IL-8 as well as increased translation of IL-8 protein resulting from this increased transcription. FIGS. 3 and 4 depict relative amounts of cytokine production mediated by TLR-2 and TLR-5 potentiated NF-kB activation. FIGS. 3(a)-3(b) depict the expression levels of interleukin-8 mRNA analyzed by RT-PCR, while FIGS. 4(a)-4(b) depict amounts (pg/ml) of interleukin-8 produced in culture medium measured by ELISA.

Heat pretreatment diminishes the ability of F301 to induce activation of intracellular NF-κB as mediated through the TLR-5 receptor, but does not diminish the ability of F331 to induce activation of intracellular NF-κB as mediated through the TLR-2 receptor. FIGS. 5(a)-(b) depict the effect of heat pretreatment on the ability of Reishi F3 fraction to facilitate TLR-2 or TLR-5 mediated activation of intracellular NF-κB. As seen in FIG. 5(a), the ability of TLR-2 to mediate F3-dependent activation of intracellular NF-κB is largely unaffected by heat treatment of Reishi F3. As seen in FIG. 5(b), the ability of TLR-5 to mediate F3-dependent activation of intracellular NF-κB is increasingly diminished by longer heat treatment of Reishi F3.

F3-dependent TLR-2 and TLR-5 mediated activation of intracellular NF-kB is inhibited specifically by antibodies specific for the TLR-2 and TLR-5 receptors. FIG. 6 depicts specific inhibition of F3-dependent, TLR-2 (FIG. 6a) or TLR-5 (FIG. 6b) mediated activation of intracellular NF-κB.

F301 is capable of inducing both TLR-2 and TLR-5 mediated activation of intracellular NF-κB, while F331, by contrast, robustly induces only TLR-2 mediated activation of intracellular NF-κB. FIG. 7 depicts specific activation of TLR-2 and/or TLR-5 mediated activation of intracellular NF-kB by specific subfractions of Reishi F3 fraction. As shown, F301 is capable of inducing both TLR-2 and TLR-5 mediated activation of intracellular NF-κB. F331, by contrast, robustly induces only TLR-2 mediated activation of intracellular NF-κB.

F301 subfractions are capable of initiating both TLR-2 and TLR-5 dependent activation of intracellular NF-κB. FIG. 8 depicts F301 subfractions capable of initiating TLR-2 and TLR-5 dependent activation of intracellular NF-κB.

F331 subfractions are capable of initiating TLR-2 dependent activation of intracellular NF-κB. FIG. 9 depicts F331 subfractions capable of initiating TLR-2 dependent activation of intracellular NF-κB.

Beta(1,3)glycan backbone fragments less than 5 kD in weight (for example, F3-H1-F3-H4) do not induce TLR-2 or TLR-5 mediated increased activation of intracellular NF-κB. FIGS. 10(a) and (b) demonstrate that beta(1,3)glycan backbone fragments less than 5 kD in weight do not induce TLR-2 or TLR-5 mediated increased activation of intracellular NF-κB.

F301 and F331 subfractions are capable of inducing TLR-2 mediated increased activation of intracellular NF-κB, regardless of whether the F301 or F331 are previously heat treated. However, heat treated F301 subfractions and F331 subfractions are less capable of inducing such TLR-5 mediated activation. FIG. 11(a) reflects that F301 and F331 subfractions are capable of inducing TLR-2 mediated increased activation of intracellular NF-κB, regardless of whether the F301 or F331 are previously heat treated FIG. 11(b) reflects that F301 subfractions are capable of inducing TLR-5 mediated activation of intracellular NF-κB and heat treated F301 subfractions and F331 subfractions are less capable of inducing such TLR5 mediated activation.

In FIG. 12 the effects of F3, F301 and F331 on IL-6 production is shown. Wild type mice and mice with TLR-2 knock out were compared. Both groups were treated with either F3, F301 or F331 for 24 hours. After treatment IL-6 production in cell culture medium was measured for each fraction or sub fraction using ELISA. In the peritoneal macrophages substantially lacking TLR-2 receptors, IL-6 production is decreased. This decrease indicates TLR-2 plays a role in mediating the effect of F3, F301 and F331 and/or in upregulation of IL-6 mediated by F3, F301 and F331.

F301 and F331 are also both capable of activating TLR4. F301 or F331 were administered to THP-1 cells in order to assess whether administration of F301 or F331 cells would stimulate THP-1 cells to produce IL-8. THP human monocytes were treated with 10 ug/ml of either TLR-2 or TLR-4 specific antibodies for 1 hour then stimulated for 24 hours with 100 ug/ml F301 (FIG. 13a) or 100 ug/ml F331 (FIG. 13b). After treatment IL-8 production in cell culture medium was measured using ELISA. Pretreatment of cells with anti-TLR4 antibody partially blocked the IL-8 production induced by F301 or F331. The effect of anti-TLR4 on F331 treated THP1 cells was less significant (FIG. 13b). HeNC2 and GG2EE are murine bone marrow derived macrophage cell line that expressed wild type TLR4 or mutant TLR4, respectively. F301 or F331 treated HeNC2 induced IL-6 production dose dependently.

When cells were treated with F301 (FIG. 14a) or F331 (FIG. 14b) at different concentrations for 24 hours. After treatment, IL-6 productions in cell culture medium were measured by using ELISA. The IL-6 productions were significantly decreased in GG2EE cells treated with F301 or F331. Consistent with antibody blocking experiment, the reduction was greater in F301 treated GG2EE cells than that of F331. (FIG. 3). Taken together, these results suggest that F331 primarily activates TLR2, whereas F301 activates TLR 2, 4 and 5.

In FIGS. 15a-c HPAEC-PAD Chromatography illustrates the differences in sugar content and type of subfractions F301 and F331 compared to Reishi Fraction F3.

Samples of sub fractions F301 and F331 were also measured by a HPAEC-PAD Chromatography for a total sugar content. The measure total sugar was the combination of fucose, glucosamine, glucose, galactose and mannose. An F301 sample as illustrated in FIG. 15(b) had a total sugar concentration of about 36.5%. An F331 sample as illustrated in FIG. 15(c) had a total sugar concentration of about 19%. By comparison an F3 sample illustrated in FIG. 15(a) had a total sugar concentration between that of F301 and F331.

The prophetic protocols: In vitro chemotaxis is performed on Transwell filter support (Corning). Collagen is coated on the sides of transfilters onto which cells will be seeded. Human intestinal epithelial cell line CaCo-2 is seeded onto Transwell filter support in inverted direction for 21 to 28 days for differentiation until transepithelial resistance is above 300 $\Omega cm^2$. F3 or it's subfractions are added at apical site of well-differentiated CaCo-2 cells for 2 days. Human neutrophils or dendritic cells isolated from fresh blood by Ficoll method are added at the basolateral site of CaCo-2 cells which have treated with F3 or it's subfractions. After 1 hour incubation in 37° and 5% CO2, the neutrophils or dendritic cells infiltrating from the basolateral site to apical site are quantified by myeloperoxidase activity or flow cytometry, respectively. Infiltration of neutrophils and dendritic cells into lamina propria of treated mice are detected in acetone fixed frozen tissue sections using biotinylated-anti-Gr1 antibody for neutrophils and biotinylated-anti-CD11c antibody for dendritic cells, followed by phycoerythrin conjugated streptavidin. Fluorescence images are detected using a confocal microscopy. (Reference: Lee et al., 2006. Methods in Molecular Biology 341: 205-215. See Chabot et al., 2007. Vaccine 25: 5348-5358. See Kucharzik et al., 2005. Gut 54: 1565-1572.)

While various exemplary implementations of the present disclosure have been described in detail, it is apparent that modifications and adaptations of those exemplary implementations will occur to those skilled in the art. However, it is to be expressly understood that such modifications and adaptations are within the spirit and scope of the present disclosure.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A method for increasing toll-like receptor mediated activation of NF-kappa B, the method comprising:
    administering a sufficient amount of a water soluble, hydrophilic subfraction (F301) of an alkaline extract of Reishi to at least one member of the group consisting of eukaryotic cells and eukaryotic cell-based organisms; and
    wherein the administered F301, increases toll-like receptor mediated activation of intracellular nuclear factor-kappa B by at least 5% when assayed by Reporter Gene Assay.

2. The method of claim 1, wherein the group consisting of eukaryotic cells and eukaryotic cell-based organisms comprises one or more of dendritic, epithelial, and monocyte cells and cellular precursors.

3. The method of claim 1, wherein the toll-like receptor mediated activation of intracellular nuclear factor-kappa B is mediated at least through the TLR-5 receptor.

4. The method of claim 1, wherein the toll-like receptor mediated activation of intracellular nuclear factor-kappa B is mediated at least through the TLR-2 receptor.

5. The method of claim 1, wherein the increase in toll-like receptor mediated activation of intracellular nuclear factor-kappa B is measured by Reporter Gene Assay.

6. A method for increasing toll-like receptor mediated activation of NF-kappa B, the method comprising:
    administering a sufficient amount of a water soluble, hydrophilic subfraction (F301) of an alkaline extract of Reishi to at least one member of the group consisting of eukaryotic cells and eukaryotic cell-based organisms; and
    wherein the administered F301 increases toll-like receptor mediated transcription of messenger RNA coding for cytokines by at least 5% when assayed by RT-PCR.

7. The method of claim 6, wherein the toll-like receptor increased transcription of messenger RNA coding for cytokines is mediated at least through the TLR-5 receptor.

8. The method of claim 6, wherein the toll-like receptor increased transcription of messenger RNA coding for cytokines is mediated at least through the TLR-2 receptor.

9. The method of any of claim 6, 7 or 8, wherein the increased toll-like receptor mediated transcription of messenger RNA coding results in an increase of mRNA coding for cytokines selected from the group consisting of interleukin-6, interleukin-8, and tumor necrosis factor-alpha.

10. The method of claim 6, wherein the increase in toll-like receptor mediated transcription of messenger RNA coding for cytokines is measured by RT-PCR.

11. A method for increasing toll-like receptor mediated activation of NF-kappa B, the method comprising:
    administering a sufficient amount of a water soluble, hydrophilic subfraction (F301) of an alkaline extract of Reishi to at least one member of the group consisting of eukaryotic cells and eukaryotic cell-based organisms; and wherein the administered F301, increases toll-like receptor mediated translation of messenger RNA to cytokines by at least 5% when assayed by ELISA.

12. The method of claim 11, wherein the toll-like receptor mediated increased translation of messenger RNA to cytokines is mediated at least through the TLR-5 receptor.

13. The method of claim 11, wherein the toll-like receptor mediated increased translation of messenger RNA to cytokines is mediated at least through the TLR-2 receptor.

14. The method of any of claim 11, 12 or 13, wherein the increased toll-like receptor mediated translation of messenger RNA to cytokines results in an increase in production of intracellular and/or extracellular cytokines selected from the group consisting of interleukin-6, interleukin-8, and tumor necrosis factor-alpha.

15. The method of claim 11, wherein the increase in toll-like receptor mediated translation of messenger RNA to cytokines is measured by ELISA.

16. A water soluble, hydrophilic subfraction (F301) of an alkaline extract of Reishi prepared by the process of:
  homogenizing tissue of a *Ganoderma lucidum*; extracting the homogenized tissue with 0.1 N NaOH aqueous alkaline solution to form a crude extract;
  subjecting the crude extract to gel filtration chromatography to form at least one fraction comprising a polysaccharide or glycopeptide component having terminal fucose residues;
  dialyzing at least one of the fractions containing a glycopeptide or polysaccharide component having a terminal fucose residue;
  precipitating the dialyzed fraction by adding ethanol to the dialyzed fraction; and
  resuspending the precipitate in an aqueous solution.

17. The method of claim 16, wherein the gel filtration chromatography is performed using a Sephacryl S-500® column and eluting with an aqueous Tris buffer solution.

18. A composition of matter consisting essentially of a water soluble, hydrophilic subfraction (F301) of an alkaline extract of Reishi, the composition comprising:
  a total sugar content of substantially 37 percent;
  fucose content of substantially 4 percent;
  glucosamine content of substantially 5 percent;
  galactose content of substantially 9 percent;
  Glucose content of substantially 74 percent; mannose content of substantially 9 percent.

* * * * *